(12) United States Patent
Choi

(10) Patent No.: US 7,160,994 B2
(45) Date of Patent: Jan. 9, 2007

(54) OSTEOCLAST-SPECIFIC GENES AND PROTEINS AND USES THEREOF

(75) Inventor: Yongwon Choi, Bryn Mawr, PA (US)

(73) Assignee: Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 10/368,087

(22) Filed: Feb. 14, 2003

(65) Prior Publication Data

US 2003/0186297 A1     Oct. 2, 2003

Related U.S. Application Data

(60) Provisional application No. 60/368,638, filed on Mar. 28, 2002.

(51) Int. Cl.
    *C07H 21/00* (2006.01)
(52) U.S. Cl. .............. 536/23.1; 435/69.1; 435/325
(58) Field of Classification Search .............. 435/325, 435/69.1
    See application file for complete search history.

(56) References Cited

U.S. PATENT DOCUMENTS

| 4,946,778 A | 8/1990 | Ladner et al. ............. 435/69.6 |
| 6,403,304 B1 * | 6/2002 | Stashenko et al. ............. 435/6 |
| 2003/0064379 A1 * | 4/2003 | Baker et al. ............. 435/6 |
| 2004/0157771 A1 * | 8/2004 | Bird et al. ............. 514/12 |

FOREIGN PATENT DOCUMENTS

| EP | 1 087 230 A1 | 9/1999 |
| WO | WO 88/00205 | 1/1988 |
| WO | WO 00/13024 | 3/2000 |

OTHER PUBLICATIONS

Ausubel et al., 1989 Current Protocols in Molecular Biology, vol. I, Green Publishing Associates, Inc. And John Wiley & Sons, Inc. N.Y.
Centrella et al., "Transforming Growth Factor : Is a Bifunctional Regulator of Replication and Collagen Synthesis in Osteoblast-enriched Cell Cultures from Fetal Rat Bone", J. Biol. Chem. 1987 262(6):2869-2874.
Hsu et al., "Tumor necrosis factor receptor family member RANK mediates osteoclast differentiation and activation induced by osteoprotegerin ligand", Proc. Natl. Acad. Sci. USA 1999 96:3540-3545.
Hunt et al., "Cellular mechanisms of bone resorption in breast carcinoma", British Journal of Cancer 2001 85(1):78-84.
Isgaard et al., "Effects of local administration of GH and IGF-1 on longitudinal bone growth in rats", Am. J. Physicl. 250 (Endocrinol. Metab. 13):E367-E372 1986.
Joyce et al., "Transforming Growth Factor-β and the Initiatior. of Chondrogenesis and Osteogenesis in the Rat Femur", J. Cell Biology 1990 110:2195-2207.
Kiebzak et al., "Bone Status of Senescent Female Fats:Chemical, Morphometric, and Biomechanical Analyses", J. Bone and Mineral Research 1988 3(4):439-446.
Kim et al., "A Novel Member of the Leukocyte Feceptor Complex Regulates Osteoclast Differentiation", J. Exp. Med. 2002 195:201-209.
Sambrook et al., Molecular Cloning 1989 Cold Spring Harbor Laboratory Press.
Slovik et al., "Restoration of Spinal Bone in Osteoporotic Men by Treatment with Human Parathyroid Hormone (1-34) and 1, 25-Dihydroxyvitamin D", J. Bone & Min. Res. 1986 1:377-381.
Chenu et al., "Transforming growth factor β inhibits formation of osteoclast-like cells in long-term human marrow cultures", Proc. Natl. Acad. Sci. USA 1988 85:5683-5687.
Kohler and Milstein, "Continuous cultures of fused cells secreting antibody of predefined specificity", Nature 1975 256:495-497.
Kozbor and Roder, "The production of monoclonal antibodies from human lymphocytes", Immunology Today 1983 4(3):72-79.
Noda and Camilliere, "In Vivo Stimulation of Bone Formation by Transforming Growth Factor-β", Endocrinology 1989 124:2991-2294.

* cited by examiner

*Primary Examiner*—Robert A. Wax
*Assistant Examiner*—Anand U. Desai
(74) *Attorney, Agent, or Firm*—Pearl Cohen Zedek Latzer, LLP; Mark S. Cohen

(57) ABSTRACT

Isolated nucleic acid and amino acid sequence for osteoclast-specific genes and proteins are provided. Methods for using these osteoclast-specific genes and proteins in the detection and isolation of osteoclasts, in production of antibodies specific to osteoclasts and to identify agents capable of modulating osteoclast function and treating diseases linked to osteoclasts are also provided.

3 Claims, No Drawings

OSTEOCLAST-SPECIFIC GENES AND PROTEINS AND USES THEREOF

This application claims the benefit of U.S. Provisional Application No. 60/368,638 filed Mar. 28, 2002.

FIELD OF THE INVENTION

The present invention provides osteoclast-specific genes and proteins. These genes and the proteins expressed thereby are useful as histological markers for detection and isolation of osteoclasts. In addition, the osteoclast-specific genes and proteins of the present invention are useful in identifying compounds which modulate the function of osteoclasts. Proteins expressed by the genes of the present invention can also be used to raise osteoclast-specific antibodies useful in targeting osteoclasts and modulating the function of osteoclasts.

BACKGROUND OF THE INVENTION

Bone is dynamic tissue that is remodeled constantly throughout life. Living bone tissue is replenished by the processes of resorption and deposition of bone matrix and minerals. This temporally and spatially coupled process, termed bone remodeling, is accomplished largely by two cell populations, the osteoclasts and osteoblasts. The remodeling process is initiated when osteoclasts are recruited from the bone marrow or the circulation to the bone surface. The matrix and minerals of the bone are subsequently replaced by osteoblasts recruited to the resorbed bone surface from the bone marrow. Resorption of bone is carried out mainly by osteoclasts, which are multinucleated cells that are formed by fusion of hematopoietic stem cells related to the mononuclear phagocyte series. Resorption of bone takes place in scalloped spaces where the osteoclasts are attached to components of the bone matrix. Osteoclasts have been linked to many diseases, including: marble disease, osteoporosis, fracture or trauma, bone metastasis, cancer, osteosarcoma, hypercalcemia and rheumatoid arthritis.

Increased osteoclast numbers and bone resorption are found in breast cancer metastasis (Hunt, et al. (2001) *Br. J. Cancer* (Scotland), 85(1):78–84).

Methods for identifying a compound useful for the treatment of bone disorders caused by osteoclast differentiation are described in EP 1087230.

Osteoclast differentiation inhibitors, such as notch ligand polypeptides, useful to treat bone disorders are disclosed in JP2001122798. TGF-beta has also been shown to stimulate proliferation and matrix synthesis of osteoblastic cells (Centrella, et al. (1987) *J. Biol. Chem.* 262:2869–2874), to inhibit the formation and activity of osteoclastic cells (Chenu, et al. (1988) *Proc. Natl. Acad. Sci. U.S.A.* 85:683–5687; Kiebzak, et al. (1988) *J. Bone Min. Res.* 3:439–446), and to stimulate local bone formation in vivo (Joyce, et al. (1990) *J. Cell. Biol.* 110:2195–2207; Noda and Camilliere (1989) *Endocrinology* 124:2991–2294). Other factors reported to stimulate bone growth include bone morphogenetic proteins (WO 88/00205), insulin-like growth factor (IGF) (Isgaard, et al. (1986) *Am. J. Physiol.* 250:E367–72), and parathyroid hormone (Slovik, et al. (1986) *J. Bone & Min. Res.* 1:377–381).

Methods for diagnosing skeletal disorders such as osteoporosis and osteoarthritis using a specific marker comprising IL-1 alpha, IL-1 beta, IL-6 and its receptor are described in WO 00/13024.

Osteoclast-specific genes and proteins have now been identified that are useful in detecting and isolating osteoclasts and identifying and producing agents which modulate osteoclast function.

SUMMARY OF THE INVENTION

An object of the present invention is to provide isolated nucleic acid sequences comprising mammalian osteoclast-specific genes selected from the group consisting of OCL-1E7, OCL-2A3 and OCL-5G10.

Another object of the present invention is to provide vectors comprising an isolated nucleic acid sequence for a mammalian osteoclast-specific gene selected from the group consisting of OCL-1E7, OCL-2A3 and OCL-5G10, as well as host cells which express these vectors.

Another object of the present invention is to provide amino acid sequences of polypeptides expressed by a mammalian osteoclast-specific gene comprising OCL-1E7, OCL-2A3 or OCL-5G10.

Another object of the present invention is to provide antibodies raised against a protein or protein fragment expressed by a mammalian osteoclast-specific gene comprising OCL-1E7, OCL-2A3 or OCL-5G10.

Another object of the present invention is to provide methods for detecting and isolating osteoclasts which comprise identifying in a biological sample cells expressing OCL-1E7, OCL-2A3 or OCL-5G10 and isolating the cells expressing OCL-1E7, OCL-2A3 or OCL-5G10.

Another object of the present invention is to provide a method for identifying modulators of osteoclast function comprising identifying agents which inhibit or activate expression of OCL-1E7, OCL-2A3 or OCL-5G10 and/or activity of proteins encoded thereby.

Yet another object of the present invention is to provide compositions comprising an agent which is targeted to OCL-1E7, OCL-2A3 or OCL-5G10 or a protein encoded thereby for use in modulating osteoclast function.

DETAILED DESCRIPTION OF THE INVENTION

The present invention is related to mammalian genes and proteins now identified to be specific to osteoclasts. In particular, three genes and the proteins encoded thereby have now been identified in both mouse and human as osteoclast-specific genes and proteins. The osteoclast-specific genes and proteins are referred to herein as OCL-1E7, OCL-2A3 and OCL-5G10. For purposes of the present invention, by "osteoclast-specific" it is meant that the highest concentrations of the gene and/or protein, were identified in osteoclasts as compared to other tissues examined including brain, liver, lung, heart, kidney, muscle, thymus, spleen, and lymph nodes and other cells derived form bone marrow.

Osteoclast-specific genes and proteins of the present invention are useful as histological markers for detection and isolation of osteoclasts. In addition, the osteoclast-specific genes and proteins of the present invention are useful in identifying compounds which modulate the function of osteoclasts via interaction with the osteoclast-specific gene or protein. Proteins expressed by the genes of the present invention or antigenic fragments thereof can also be used to raise osteoclast-specific antibodies useful in targeting osteoclasts and modulating the function of osteoclasts.

Osteoclast-specific genes of the present invention were identified via probing of a cDNA array with cDNAs from osteoclasts and/or macrophages. The cDNA array with subtracted cDNA library was constructed using the PCR-select subtraction kit according to manufacturer's protocol (CLONTECH™, Palo Alto, Calif.). Gene fragments with a higher apparent expression in osteoclasts as compared to macrophages were used for northern analysis. Among these gene fragments, the cDNA fragments for OCL-1E7, OCL-2A3 and OCL-5G10 were identified.

Accordingly, one embodiment of the present invention relates to isolated nucleic acid sequences and amino acid sequences for the mammalian osteoclast-specific gene and polypeptide, respectively, referred to herein as OCL-1E7. A murine OCL-1E7 fragment was used to obtain full-length murine OCL-1E7. An isolated nucleic acid sequence for full-length murine OCL-1E7 is provided as SEQ ID NO:1 and the amino acid sequence for a murine OCL-1E7 polypeptide encoded thereby is provided as SEQ ID NO:10. Murine OCL-1E7 was then used to isolate human OCL-1E7 orthologs by screening a cDNA library derived from monocyte-derived osteoclasts. An isolated nucleic acid sequence for a long form of human OCL-1E7 is provided as SEQ ID NO:2 and the amino acid sequence for a polypeptide encoded by the long form of human OCL-1E7 is provided as SEQ ID NO:11. A short form of human OCL-1E7 with a premature stop codon was also identified. An isolated nucleic acid sequence for a short form of human OCL-1E7 is provided as SEQ ID NO:3 and the amino acid sequence for a polypeptide encoded by the short form of human OCL-1E7 is provided as SEQ ID NO:12. Only portions of this gene have been disclosed in human genomic databases. Comparison of murine and human OCL-1E7 indicates 78.3% amino acid identities. Amino acid analysis also revealed a bona fide domain for a sodium-hydrogen (Na—H) exchanger at amino acids 176–503 of SEQ ID NO:11. However, OCL-1E7 is significantly different from other mammalian proteins identified in the Na—H exchange family of proteins.

To demonstrate the specificity of OCL-1E7 to osteoclasts, mRNA derived from osteoclasts and macrophages was hybridized with $^{32}$P-labeled OCL-1E7. mRNA expression was detected in bone-marrow-derived osteoclasts, but not in bone-marrow-derived macrophages. OCL-1E7 expression was also undetectable in bone-marrow-derived dendritic cells (DCs), another cell type derived from the same precursor as osteoclasts and macrophages. mRNA expression of OCL-1E7 was also undetectable in RNA derived from brain, liver, lung, heart, kidney, muscle, thymus, spleen and lymph node.

RAW264.7 cells can be differentiated into osteoclast-like cells by treatment with TNF-related activation induced cytokine (TRANCE; Wong, et al. (1997) *J. Biol. Chem.* 272:25910–25914). Accordingly, expression of OCL-1E7 was also examined in these cells. It was found that OCL-1E7 expression was detectable 48 hours after stimulation of RAW264.7 cells. Further expression was highest 4 days after TRANCE stimulation when RAW264.7 cells were completely differentiated in osteoclasts.

Human monocytes can also be differentiated into osteoclast-like cells in vitro by stimulation with macrophage-colony stimulating factor (M-CSF) and TRANCE. Accordingly, expression of OCL-1E7 was also examined in these cells. It was found that OCL-1E7 expression was detectable in the differentiated human osteoclast-like cells but not in the monocyte precursors.

This demonstrated specificity of OCL-1E7 for osteoclasts is indicative of this gene and the polypeptide encoded thereby being useful in the detection of osteoclasts in tissue samples.

Further, OCL-1E7 can be used to isolate osteoclasts from mixed populations of cells.

The presence of the Na—H exchanger domain in OCL-1E7 is indicative of OCL-1E7 being a regulator of the bone resorptive function of osteoclasts. Accordingly, agents which modulate expression of OCL-1E7 and/or activity of the polypeptide encoded thereby are expected to be useful in modulating the function of osteoclasts.

Another embodiment of the present invention relates to isolated nucleic acid sequences and amino acid sequences for the mammalian osteoclast-specific gene and polypeptide, respectively, referred to herein as OCL-2A3. Murine OCL-2A3 fragment was used to obtain full-length murine OCL-2A3 by screening a cDNA library derived from bone-marrow derived murine osteoclasts. Two forms of cDNAs for OCL-2A3 with identical open reading frames were identified (see SEQ ID NO:4 and SEQ ID NO:5). An amino acid sequence of murine OCL-2A3 polypeptide is provided as SEQ ID NO:13. Murine OCL-2A3 was used to isolate human OCL-2A3 orthologs by screening a cDNA library derived from monocyte-derived human osteoclasts. Two forms of full-length human cDNA sequences with identical open reading frames were also identified and provided as SEQ ID NO:6 and SEQ ID NO:7. An amino acid sequence of human OCL-2A3 polypeptide is provided as SEQ ID NO:14. Only portions of human OCL-2A3 genomic sequences have been revealed in human genome data bases. Comparison of murine and human OCL-2A3 amino acid sequences indicate 93.1% amino acid identities. Amino acid analysis of OCL-2A3 indicates that mouse OCL-2A3 shows 67.4% amino acid identities or homology to a previously identified murine protein ATPaseD (GENBANK® Accession No. AAA92288.1). Human OCL-2A3 also showed 66.9% amino acid identities or homology to a previously identified human ATPaseD (GENBANK® Accession No. CAA50591.1). OCL-2A3 also shows significant homologies (greater than 60%) to ATPaseD from other species. Thus, OCL-2A3 encodes for an osteoclast-specific ATPaseD-like subunit of the multisubunit vacuolar-like H$^+$-ATPase (V-ATPase), the proton pump required for bone resorption by osteoclasts.

To demonstrate specific expression of OCL-2A3 in osteoclasts, mRNA derived from osteoclasts and macrophages was hybridized with $^{32}$P-labeled OCL-2A3. mRNA expression analysis predominantly detected expression that was in bone-marrow-derived osteoclasts. Only low levels of mRNA expression were detected in bone-marrow-derived macrophages and dendritic cells and OCL-2A3 expression was undetectable in RNA derived from brain, liver, lung, heart, kidney, muscle; thymus, spleen, and lymph nodes, thus indicating that OCL-2A3 expression is highly enriched in osteoclasts. In contrast, a previously reported ATPaseD was found in these experiments to be ubiquitously expressed in various tissues.

mRNA expression profiling of various subunits of vacuolar-like H$^+$-ATPase were also measured among osteoclasts, macrophages, and dendritic cells, and showed OCL-2A3 expression to be most restricted to osteoclasts.

OCL-2A3 expression was also detected 48 hours after stimulation of RAW264.7 cells to differentiate into osteoclast-like cells, and its expression was highest when these cells were completely differentiated into osteoclast-like cells (4 days after TRANCE stimulation). Unlike OCL-2A3, ATPaseD is constitutively expressed before and after differentiation of RAW264.7 cells. Other subunits of V-ATPases were also expressed constitutively before and after differentiation of RAW264.7 cells.

This demonstrated that specificity of OCL-2A3 for osteoclasts is indicative of this gene and the polypeptide encoded thereby being useful in the detection of osteoclasts in tissue samples.

Further, OCL-2A3 can be used to isolate osteoclasts from mixed populations of cells.

The homology of OCL-2A3 to ATPaseD is indicative of OCL-2A3 being an ATPaseD-like subunit in the multisubunit vacuolar-like H$^+$-ATPase subunit. Multisubunit vacuolar-like H$^+$-ATPase subunit functions as the proton pump required for bone resorption by osteoclasts. Accordingly, agents which modulate expression of OCL-2A3 and/or activity of the polypeptide encoded thereby are expected to be useful in modulating the function of osteoclasts.

In yet another embodiment of the present invention, isolated nucleic acid sequences and amino acid sequences are provided for the mammalian osteoclast-specific gene and polypeptide, respectively, referred to herein as OCL-5G10. A murine OCL-5G10 fragment was used to obtain a full-length murine OCL-5G10 by screening a cDNA library derived from bone-marrow-derived murine osteoclasts. An isolated nucleic acid sequence for the full-length murine OCL-5G10 is provided as SEQ ID NO:8 and the amino acid sequence for a murine OCL-5G10 polypeptide encoded thereby is provided as SEQ ID NO:15. Murine OCL-5G10 was used to isolate human OCL-5G10 orthologs by screening a cDNA library derived from monocyte-derived human osteoclasts. An isolated nucleic acid sequence for human OCL-5G10 is provided as SEQ ID NO:9 and the amino acid sequence for a human OCL-5G10 polypeptide encoded thereby is provided as SEQ ID NO:16. Only portions of this gene have been disclosed in human genomic databases. Comparison of murine and human OCL-5G10 indicate 84.2% amino acid identities. Amino acid analysis of OCL-5G10 indicates that it contains a bona fide von Willebrand factor (vWF) type A domain at amino acid 44 through 412. vWF domains in extracellular eukaryotic proteins mediate adhesion and are found in integrin beta subunits. Recently, BLAST analysis identified a close homolog of human OCL-5G10 as CMG-2. CMG-2 was identified during mRNA profile analysis of in vitro model of human capillary tube formation (Bell, et al. (2001) *J. Cell. Sci.* 114:2755–2773). However, both amino acid and cDNA comparison between OCL-5G10 and CMG-2 shows that they are significantly different.

To demonstrate specific expression of OCL-5G10 in osteoclasts, mRNA derived from osteoclasts and macrophages was hybridized with $^{32}$P-labeled OCL-2A3. mRNA expression was predominantly detected in bone-marrow-derived osteoclasts, and not in bone-marrow-derived macrophages and dendritic cells. OCL-5G10 expression was also detected 48 hours after stimulation of RAW264.7 cells to differentiate to osteoclast-like cells, and its expression was highest when RAW264.7 cells were completely differentiated into osteoclasts (4 days after TRANCE stimulation). In addition, OCL-5G10 mRNA was detected in human monocyte-derived osteoclasts, but not in monocyte precursors.

The only other tissue examined wherein OCL-5G10 mRNA expression was high was the heart.

This demonstrated specificity of OCL-5G10 for osteoclasts is indicative of this gene and the polypeptide encoded thereby being useful in the detection of osteoclasts in tissue samples.

Further, OCL-5G10 can be used to isolate osteoclasts from mixed populations of cells.

The vWF domain has been implicated in various integrin-mediating cell-cell interactions and cell-extracellular matrix interactions. Thus, its presence in OCL-5G10 is indicative of OCL-5G10 being involved in these interactions. Accordingly, agents which modulate expression of OCL-5G10 and/or activity of the polypeptide encoded thereby are expected to be useful in modulating integrin-mediating cell-cell and cell extracellular matrix interactions of osteoclasts.

The present invention also relates to vectors which include osteoclast-specific nucleic acid sequences of the present invention, host cells which are genetically engineered with vectors of the invention and the production of polypeptides of the invention by recombinant techniques. Host cells can be genetically engineered to incorporate nucleic acid sequences and express polypeptides of the present invention using well-known techniques such as infection, transduction, transfection, and transformation. The osteoclast-specific nucleic acid sequences can be introduced alone or with other polynucleotides introduced independently, co-introduced or introduced joined to the nucleic acid sequences of the present invention. For example, an osteoclast-specific nucleic acid sequence of the present invention may be transfected into host cells with another, separate, polynucleotide encoding a selection marker, using standard techniques for co-transfection and selection in the host cell. Alternatively, an osteoclast-specific nucleic acid sequence may be joined to a vector containing a selectable marker for propagation in a host and introduced into host cells by any of the aforementioned techniques. A great variety of expression vectors, promoters and host cells are available for expression of a polypeptide of the present invention. Selection of appropriate vectors and promoters for expression in a host cell is a well-known procedure and the expression vector construction, introduction of the vector into the host and expression in the host are routine skills in the art.

Detection and/or isolation of osteoclasts via the osteoclast-specific nucleic acid sequences or polypeptides of the present invention can be performed in accordance with well-known techniques. Examples of methods useful for detection of an osteoclast-specific nucleic acid sequence of the present invention indicative of osteoclasts in the sample include, but are not limited, polymerase chain reaction (PCR), ligase chain reaction (LCR) and nucleic acid sequence based amplification (NASABA). Reverse-transcriptase PCR (RT-PCR) is also a powerful technique which can be used to detect the presence of specific mRNA populations in a complex mixture of thousands of other mRNA species. In RT-PCR, an mRNA species is first reverse transcribed to complementary DNA (cDNA) with use of the enzyme reverse transcriptase; the cDNA is then amplified as in a standard PCR reaction. RT-PCR can thus reveal by amplification the presence of a single species of mRNA. Hybridization to clones or oligonucleotides arrayed on a solid support (i.e. gridding) can also be used to detect the presence of an osteoclast-specific nucleic acid sequence of the present invention.

Methods for detecting the presence or absence of a known polypeptide sequence are also well-known in the art and can be adapted routinely to detect an osteoclast-specific polypeptide of the present invention. An osteoclast-specific polypeptide of the present invention or an antigenic fragment thereof can be used to raise antibodies against the osteoclast-specific polypeptide. Such antibodies can then be used in various assays to detect the presence or absence of the polypeptide in a sample. Examples of these assays include, but are not limited to, radioimmunoassays, immunohistochemistry assays, competitive-binding assays, Western Blot analyses, ELISA assays, proteomic approaches, two-dimensional gel electrophoresis (2D electrophoresis) and non-gel based approaches such as mass spectrometry or protein interaction profiling.

The present invention also provides antibodies specific to the osteoclast-specific polypeptides of the present invention. These osteoclast-specific antibodies have a variety of uses including, but not limited to, use in methods for detecting and isolating osteoclasts as well as targeting agents to osteoclasts. The osteoclast-specific polypeptides of the present invention or their fragments or variants thereof, or cells expressing them can be used as immunogens to produce antibodies immunospecific for the osteoclasts. The term "immunospecific" means that the antibodies have substantially greater affinity for cells expressing the osteoclast-specific polypeptides of the present invention as compared to their affinity for other related polypeptides in the prior art. These antibodies can be polyclonal or monoclonal. In addition, by the term "antibody", it is meant to include chimeric, single chain and humanized and fully human antibodies as well as Fab fragments or products of Fab expression libraries.

Antibodies generated against the osteoclast-specific polypeptides can be obtained by administering the polypeptides or epitope-bearing fragments, variants or cells to an animal, preferably a nonhuman, using well-known techniques. For preparation of monoclonal antibodies, any technique which provides antibodies produced by continuous cell line cultures can be used. Examples include the hybridoma technique (Kohler, G. and Milstein, C., *Nature* (1975) 256:495–497), the trioma technique, the human B-cell hybridoma technique (Kozbor et al., *Immunology Today* (1983) 4:72) and the EBV-hybridoma technique (Cole et al., MONOCLONAL ANTIBODIES AND CANCER THERAPY, pp. 77–96, Alan R. Liss, Inc., 1985).

Techniques for the production of single chain antibodies (U.S. Pat. No. 4,946,778) can also be adapted to produce single chain antibodies to polypeptides of this invention. Also, transgenic mice, or other organisms including other mammals, can be used to express humanized antibodies.

The above-described antibodies can be used to isolate or to identify osteoclasts expressing the osteoclast-specific polypeptides and to purify osteoclasts expressing the polypeptides by various methods well know in the art, including, but in no way limited to, flow cytometry. Antibodies against osteoclast-specific polypeptides can also be used to target selected molecules to osteoclasts. Examples of molecules which can be linked to an osteoclast-specific antibody of the present invention include, but are not limited, DNA, toxins, imaging agents, and therapeutic agents which modulate a function of osteoclasts.

Antibodies which can be used in in vivo methods include polyclonal, monoclonal and omniclonal antibodies and antibodies prepared via molecular biology techniques. Antibody fragments and aptamers and single-stranded oligonucleotides such as those derived from an in vitro evolution protocol referred to as SELEX and well-known to those skilled in the art can also be used.

The osteoclast-specific nucleic acid sequences and polypeptides of the present invention also provide useful tools for development of agents which modulate osteoclast function. The nucleic acid sequence and/or polypeptides can be used to identify agents which alter expression and/or activity of the osteoclast-specific polypeptides. Such agents can be identified in routine screening assays which examine levels of the osteoclast-specific genes or polypeptide encoded thereby. Agents identified as altering levels and/or expression of an osteoclast-specific gene or polypeptide of the present invention are expected to be useful in modulating osteoclast function.

Agents comprising small molecules predicted via computer imaging to specifically bind to regions of osteoclast-specific polypeptides can also be designed, synthesized and tested for use in modulating osteoclast function. Further, libraries of molecules can be screened for potential osteoclast modulating agents by assessing the ability of the molecule to bind to the osteoclast-specific polypeptides identified herein. Molecules identified in the library as being capable of binding to osteoclast-specific polypeptides are key candidates for further evaluation for use in modulating osteoclast function. In a preferred embodiment, these molecules will modulate expression and/or activity of osteoclast-specific polypeptides in cells.

Agents identified as modulators of expression and/or activity of osteoclast-specific polypeptide are expected to be useful in the treatment of diseases linked to osteoclasts. Examples of such diseases include, but are not limited to, marble disease, osteoporosis, fracture or trauma, bone metastasis, cancer, osteosarcoma, hypercalcemia and rheumatoid arthritis.

For purposes of the present invention, by "osteoclast-specific nucleic acid sequence" it is meant to include the nucleic acid sequences of OCL-1E7, OCL-2A3 and OCL-5G10 exemplified as SEQ ID NOs:1 through 9, and any nucleic acid sequence that hybridizes thereto under moderately stringent conditions. By "moderately stringent conditions" it is meant conditions such as those described by Ausubel, et al. ((1989) Current Protocols in Molecular Biology, Vol. I, Green Publishing Associates, Inc. and John Wiley & Sons, Inc. N.Y.). By "nucleic acid sequence" it is also meant to encompass degenerate variants encoding the same polypeptides or polypeptides with similar activities to those provided as SEQ ID NOs:10 through 16. By nucleic acid sequence it is meant to include both genomic DNA or cDNA and mRNA transcribed by the genomic DNA.

By "isolated" for purposes of the present invention, it is meant that the nucleic acid sequence or polypeptide is substantially separated from other cellular components that naturally accompany the native nucleic acid sequence or polypeptide in a host cell from which it is naturally associated. The term includes nucleic acid sequences and polypeptides that have been removed from their naturally occurring environment, are no longer associated with all or a portion of a polynucleotide or polypeptide in which the "isolated" nucleic acid sequence or polypeptide is found in nature, are operatively linked to a polynucleotide or polypeptide which they are not linked to in nature or contain nucleotides or internucleoside bonds or modified peptides that are not found in nature. Thus, the term "isolated" as used with respect to nucleic acid sequences is meant to be inclusive of nucleic acid molecules that are integrated into a host cell chromosome at a heterologous site, recombinant fusions of a native fragment to a heterologous sequence, and recombinant vectors present as episomes or as integrated into a host cell chromosome. In addition, a nucleic acid sequence of the present invention may include either or both naturally-occurring and modified nucleotides linked together by naturally-occurring and/or non-naturally occurring nucleotide linkages. The nucleic acid molecules may be modified chemically or biochemically or may contain non-natural or derivatized nucleotide bases, as are well know by those of skill in the art.

By "gene" as used herein it is meant a nucleic acid sequence that encodes a polypeptide and the expression control sequences that surround the nucleic acid sequence that encodes the polypeptide. For example, a gene may comprise a promoter, one or more enhancers, a nucleic acid sequence that encodes a polypeptide, downstream regulatory sequences and, possibly, other nucleic acid sequences involved in regulation of the expression of an RNA.

The following nonlimiting examples are provided to further illustrate the present invention.

EXAMPLES

Example 1

Probing of cDNA Array

Poly A+ RNA (0.5 µg) was labeled with Cy3 or Cy5 mono-reactive dyes (Amersham/Pharmacia, Piscataway, N.J.) using ATLAST™ glass fluorescent labeling kit (CLONTECH™, Palo Alto, Calif.) following the manufacturer's protocol with the following modifications. The labeled Cy3 or Cy5 probes were purified with PROBEQUANT™ G-50 purification kit (Amersham/Pharmacia). The purified probes were dried and resuspended in 20 µl of hybridization solution (25% formamide, 5×SSC, 0.1% SDS, 10 µg of ssDNA). The array was cross-linked with 200 mJoules of UV-irradiation and incubated with pre-hybridization solution (25% formamide, 5×SSC, 0.1% SDS, and 10 mg/ml of BSA) at 42° C. for 45 minutes in a Colpin jar. After the pre-hybridization, the array was rinsed once with distilled water and 100% ethanol. The array was dried and kept at room temperature until hybridization. The probes were denatured at 99° C. for 2 minutes, cooled on ice, and centrifuged. The supernatant was applied onto the array and covered with cover glass in a CORNING® hybridization chamber. Hybridization was performed at 42° C. for 18 hours. The slides were then washed once with 2×SSC-0.1% SDS at 42° C. for 5 minutes, once with 0.1×SSC-0.1% SDS at room temperature for 10 minutes, and four times with 0.1×SSC at room temperature for 1 minute. Finally, the slides were washed with distilled water, ethanol, and then dried. Arrays were scanned with a GMS 418 Array Scanner (AFFYMETRIX®, Santa Clara, Calif.).

Example 2

Isolation of Full-length Murine and Human Sequences

Mouse osteoclast and human osteoclast cDNA libraries (Kim, et al. (2002) *J. Exp. Med.* 195:201–209) were generated using polyA mRNA from bone marrow-derived mature osteoclast cells according to manufacture's protocol (STRATAGENE®, La Jolla, Calif.). The full-length cDNAs for OCL1E7, OCL2A3 and OCL5G10 were isolated from mouse osteoclast and human osteoclast cDNA libraries (Kim, et al. (2002) supra) using the inserts containing the fragment of those genes as described Sambrook et al. ((1989) Molecular cloning, Cold Spring Harbor Laboratory Press).

Example 3

Northern Blot Analysis

Northern blot analysis was performed using northern hybridization buffer (50% formamide, 50 mM sodium phosphate, pH 6.8, 5× Denhardt's solution, 5×SSC, 3 mg/ml sonicated salmon sperm DNA) as described by Sambrook et al. ((1989) supra). The total RNA from the different cell types and tissue samples were harvested using TRIZOL®. The tissues were homogenized in TRIZOL® using homogenizer and the total RNAs were harvested according to manufacturer's protocol (GIBCO™, Carlsbad, Calif.)

Example 4

Differentiation of Raw264.7 Cells

Raw 264.7 cells can be differentiated into OC-like cells by treatment of TRANCE as described by Hsu, et al. ((1999) *Proc. Natl Acad. Sci* 96:3540–3545).

---

What is claimed is:

1. An isolated mammalian osteoclast-specific nucleic acid sequence comprising SEQ ID NO:1, SEQ ID NO:2, or SEQ ID NO:3.

2. A vector comprising the isolated mammalian osteoclast-specific nucleic acid sequence of claim 1.

3. A purified host cell comprising the vector of claim 2.

SEQUENCE LISTING

```
<160> NUMBER OF SEQ ID NOS: 16

<210> SEQ ID NO 1
<211> LENGTH: 1987
<212> TYPE: DNA
<213> ORGANISM: Mus musculus

<400> SEQUENCE: 1
ggaagccagg aggcctgcgc agactgccag caatgagagc agctctggct cctcatccct      60
gagtcatcat cttcgaaatt ataagacatg gaggatgaag ataagacagc tgaatgtcag     120
cattcaaagc cacctacggg gatcacacac gaggctcctc cacatcacga actacaggaa     180
gagagagtca tgagcctcag aggtacagac agaagtgaac cgacagaagg cagtaacctg     240
ctgaccagcg gtgaaaaaaa gccacaggac tcaccaacag aacccaatgg cctgcagagt     300
ctgaggcgat tcctggcctg ccctccacga ggctgcctgg caagagtgat aacgaacggt     360
accatggttt ttcttctgtg ggccatggtt tggtcagtta ccggccctga atgtcttcct     420
ggaggaaatc tgtttggaat tatcattctg ttctattgtt ccatcaccgg aggtaaactt     480
```

-continued

```
tttggactca ttaagtttcc aacattgcct cctctgcctc ctcttcttgg catgctgcta      540
gctgggtttc tcttgaggaa tatcccagtc atcaatgata gcgtccggat ccaacacaag      600
tggtcgtcat ctttgagaag catagccctt tctgtcattc tggttcgtgc tggccttggt      660
ctagattcaa aggccctgag gaagctgaag ggtgtgtgtg tgcgactggc catgggtccc      720
tgcatcgtgg aggcgtgtgc ttctgcgatt ctctcacact tcctgatggg gttgccatgg      780 caatggggt tcatcctggg ttttgtcgta ggtgccgtgt ccccagctgt cgtggtgccc       840
tccatgctcc ttttgcagga aggaggctac ggtgttggaa aaggtatccc aaccttactc      900
atggccgccg gcagcttcga tgacatcctg gccatcactg gcttcaacac gtgcttaggc      960
gtggcctttt ccacaggatc tacagttttt aacatcttca gaggcatctt ggaggtggta     1020
attggtgtgg cagctggatc ttttcttggg ttttttatcc agtacttccc gagcagggac     1080
caggacaacc tcgtgtggaa gcgagccttt ctggttctgg gttttgctgt gctcgctgtg     1140
ttcagcagtg tgtattttag cttcccgggg tctggaggac tctgcacgtt ggtcatggct     1200
ttcctagcag gcatgaggtg gactgacaag aagtcagagg tagaaaaggt cattgcagtt     1260
acctgggacg ttttccagcc tcttcttttt ggcctgattg gagcagaggt ttccattgtg     1320
tctctcagag cagaaacggt tggcctttgt gttgcaaccc tcagcatcgc agtgcttata     1380
cgaattctga ctacattcct gatggtgtgt ttcgctggct ttaacataaa ggaaaagata     1440
tttatttctt ttgcctggct tccaaaggcc acggtccagg ctgccattgg ctctgtggct     1500
ctggacacgg caagatccca cggagagaag cagctggaaa actatgggat ggatgtgctg     1560
acggtggcat ttttggccat cctcattaca gcaccaattg gaagcctact gattggtttg     1620
ctgggtccca gggttcttca gaaatctgaa catcgaaccg aagaggaggt tcaaggagag     1680
acttctgcac acattcagag gaagcctgag gattccatta cggaagcctg atggaccatg     1740
tttaccatcc caacccaaag gttttggccc tccaacaacc gggacaactt tacttccctt     1800
tgactcagaa gaaaacttcc cgtggaattt cataagcaaa caaattagaa agctttacgc     1860
tgctaacagt acctcaggtg tttacttcct cagaaagacc ggaggacagg ttacttcaga     1920
aagtgagaga aagtaatttg gacaaataaa acattcacga ttttgttaaa aaaaaaaaa      1980 aaaaaaa                                                                1987
```

<210> SEQ ID NO 2
<211> LENGTH: 1894
<212> TYPE: DNA
<213> ORGANISM: Homo sapiens

<400> SEQUENCE: 2

```
ccttgcttga aaagcggtga ttaagattgg cacttgctta caggagtgaa aaacagatct      60
cgttcctctt ccctgtgtca tcttcttaat tataaataat gggggatgaa gataaaagaa     120
ttacatatga agattcagaa ccatccacag gaatgaatta cacgccctcc atgcatcaag     180
aagcacagga ggagacagtt atgaagctca aaggtataga tgcaaatgaa ccaacagaag     240
gaagtattct tttgaaaagc agtgaaaaaa agctacaaga aacaccaact gaagcaaatc     300
acgtacaaag actgagacaa atgctggctt gccctccaca tggtttactg gacagggtca     360
taacaaatgt taccatcatt gttcttctgt gggctgtagt ttggtcaatt actggcagtg     420
aatgtcttcc tggaggaaac ctatttggaa ttataatcct attctattgt gccatcattg     480 gtggtaaaact ttggggctta ttaagttacc tacattgcct ccactgcctt ctcttcttgg     540
```

-continued

| | |
|---|---|
| gcatgctgct tgcagggttt ctcatcagaa atatcccagt catcaacgat aatgtgcaga | 600 |
| tcaagcacaa gtggtcttcc tcttttgagaa gcatagccct gtctatcatt ctggttcgtg | 660 |
| ctggccttgg tctggattca aaggccctga agaagttaaa gggcgtttgt gtaagactgt | 720 |
| ccatgggtcc ctgtattgtg gaggcgtgca catctgctct tcttgcccat tacctgctgg | 780 |
| gtttaccatg gcaatgggga tttatactgg gttttgtttt aggtgctgta tctccagctg | 840 |
| ttgtggtgcc ttcaatgctc cttttgcagg gaggaggcta tggtgttgag aagggtgtcc | 900 |
| caaccttgct catggcagct ggcagcttcg atgacattct ggccatcact ggcttcaaca | 960 |
| catgcttggg catagccttt tccacaggct ctactgtctt taatgtcctc agaggagttt | 1020 |
| tggaggtggt aattggtgtg gcaactggat ctgttcttgg attttttcatt cagtactttc | 1080 |
| caagccgtga ccaggacaaa cttgtgtgta agagaacatt ccttgtgttg gggttgtctg | 1140 |
| tgctagctgt gttcagcagt gtgcattttg gtttccctgg atcaggagga ctgtgcacgt | 1200 |
| tggtcatggc tttccttgca ggcatgggat ggaccgaccg cgaaaaggca gaggttgaaa | 1260 |
| agataattgc agttgcctgg acatttttc agccccttct ttttggacta attggagcag | 1320 |
| aggtatctat tgcatctctc agaccagaaa ctgtaggcct ttgtgttgcc accgtaggca | 1380 |
| ttgcagtatt gatacgaatt ttgactacat ttctgatggt gtgttttgct ggttttaact | 1440 |
| taaaagaaaa gatatttatt tcttttgcat ggcttccaaa ggccacagtt caggctgcaa | 1500 |
| taggatctgt ggctttggac acagcaaggt cacatggaga gaaacaatta gaagactatg | 1560 |
| gaatggatgt gttgacagtg gcatttttgt ccatcctcat cacagcccca attggaagtc | 1620 |
| tgcttattgg tttactgggc cccaggcttc tgcagaaagt tgaacatcaa aataaagatg | 1680 |
| aagaagttca aggagagact tctgtgcaag tttagaggaa gcgcggattc tattactgga | 1740 |
| aactttggga ctgaaaggcc aaagcttctg ggcccaccat caacgcagct ccgctttcat | 1800 |
| ttctttcaca tacaactttc cacataagat ttcatgcgga aaaaaaaaaa aaaactcaca | 1860 |
| aaggttttat actgataaaa aaaaaaaaaa aaaa | 1894 |

<210> SEQ ID NO 3
<211> LENGTH: 1915
<212> TYPE: DNA
<213> ORGANISM: Homo sapiens

<400> SEQUENCE: 3

| | |
|---|---|
| gtattggatg gaacctatcc aataggttca tcacaaaaga ggacctgaga gacaagaatg | 60 |
| aatggttct gactggtgga gaaatttgag gataatctcc cttgcttgaa aagcggtgat | 120 |
| taagattggc acttgcttac aggagtgaaa aacagatctc gttcctcttc cctgtgtcat | 180 |
| cttcttaatt ataaataatg ggggatgaag ataaagaat tacatatgaa gattcagaac | 240 |
| catccacagg aatgaattac acgccctcca tgcatcaaga agcacaggag gagacagtta | 300 |
| tgaagctcaa aggtatagat gcaaatgaac caacagaagg aagtattctt ttgaaaagca | 360 |
| gtgaaaaaaa gctacaagaa acaccaactg aagcaaatca cgtacaaaga ctgagacaaa | 420 |
| tgctggcttg ccctccacat ggtttactgg acagggtcat aacaaatgtt accatcattg | 480 |
| ttcttctgtg ggctgtagtt tggtcaatta ctggcagtga atgtcttcct ggaggaaacc | 540 |
| tatttggaat tataatccta ttctattgtg ccatcattgg tggtaaactt ggggcttat | 600 |
| taagttaccct acattgcctc cactgccttc tcttcttggg catgctgctt gcagggtttc | 660 |
| tcatcagaaa tatcccagtc atcaacgata atgtgcagat caagcacaag tggtcttcct | 720 |
| cttttgagaag catagccctg tctatcattc tggttcgtgc tggccttggt ctggattcaa | 780 |

```
aggccctgaa gaagttaaag ggcgtttgtg taagactgtc catgggtccc tgtattgtgg      840
aggcgtgcac atctgctctt cttgcccatt acctgctggg tttaccatgg caatggggat      900
ttatactggg gtaatgattg tttctttgtc atatgaaaat atgtagggac atttagggct      960
ttccctgatt gcatacaaga gaatgcataa tagaattttc ttatagatat cagaaaatgc     1020
aacatagatg ttcagcata atttaaatat tctaacttca aaacatagtt tatgtgttaa      1080
taggcgctaa ctcttacagt tagcacctac tattcaaact gttgaagaag tcgtggtctt     1140
ttgcctacac ctgattcaat gcctgttaaa gagataccgg attccaccta acgtctgcac     1200
aaaggataat aaacacagca acagtgatca acagctacta ttgttttcct cctgtcacca     1260
gactattatg acttggcagt tctgctgtct cttcgttcca ctgtcagttc tttacttcca     1320
acagttaaga gccacacaaa gtaaataaat aagacaggac ttagtaagaa tttagtgcta     1380
ataagaggca agaagtaaga aattcttctc atggttaagt ctctggaact ctactccctg     1440
gattcaaatc ccagcctgtg attttccgg  tgtgtgatct ttaacaagta tttaatctct     1500
ctgtgcctca gtttcctcaa ttataaaatt aagatagatt ttgtctattt tatagggttg     1560
ttgtgaggat taaattagtg aatacgtgta aagtgctcaa aatggtgtct ggtacatagt     1620
aaatactgta aaatgctttc tgctgttacc actgctgttg ttactggtat caatgtgact     1680
gtcatatcgt tttcttctaa tctgttgcct tatttgacat agcaagccct aatagaaggc     1740
ctagcatcac tgggttccaa atcagaaagt ccatgcattt tcaaacctta taacatgaat     1800
ttttttgttt aaaaaagcca gcatcctggg gcctaccctc attaggcctt ctataccact     1860
aataaatata tcttttttagg caacctaaaa aaaaaaaaaa aaaaaaaaa aaaaa           1915

<210> SEQ ID NO 4
<211> LENGTH: 1410
<212> TYPE: DNA
<213> ORGANISM: Mus musculus

<400> SEQUENCE: 4
aggactcgga gccacttcag cctgagcagt atgcttgaga ctgcagagct gtacttcaat       60
gtggaccatg gctacctgga gggcctggtt cgaggatgca agccagcct  cctaactcag      120 caggactatg tcaacctagt gcagtgtgag accttggaag acctgaaaat tcatctccag      180
accacggact atggcaactt cctggctaat gaaacaaatc ctctcactgt ttccaaaatt      240
gacacggaga tgaggaagaa gctctgcaga gagtttgact atttccggaa tcattccttg      300
gagcccctga gcacatttct cacctacatg acatgcagct atatgataga caatataatt      360
ctacttatga atggggcctt gcaaaagaaa tctgtgaaag aagttctagc caagtgtcac      420
ccactgggcc gtttcacaga gatggaagct gtcaacattg cagagacccc ctcagatctc      480
ttcaaggctg tgctggttga acaccatta  gctccattct ttcaagattg tatgtctgaa      540
aacactcttg atgaactgaa tattgaatta ctgcgcaata actatacaa  gtcttacctt      600 gaggcattct acaaattctg caaggatcac ggtgatgtca cagcagacgt tatgtgtccc      660
attcttgagt ttgaggccga cagacgcgct ttaatcatca ctctgaactc atttggcact      720
gaactaagca agaagacag  ggagaccctc ttccccacct gcggcaggct ctatccagag      780
gggttgcggt tgttagctca agctgaagac tttgagcaga tgaagagagt ggcagataat      840
tatggagttt acaagccttt gtttgacgct gtcggtggca gtgggggaa  gacactggaa      900 gacgttttct atgagagaga ggtacagatg aatgtgctgg cattcaacag gcaattccat      960
```

| | |
|---|---:|
| tatggtgtgt tttatgcgta tgtaaagttg aaggagcaag agatgagaaa tatcgtgtgg | 1020 |
| atagcagaat gcatctcaca gaggcatcga actaaaatca acagctacat tccaatttta | 1080 |
| taagccagtg tacagaagat catacatgtt gccatgaagt tattgaggaa aggaaggggg | 1140 |
| attgtgtcac attatctaga ttatataaaa gtaagtcata ccacctttcc ataaactaca | 1200 |
| tgtccactgg aagcccaagt aaacagaact tgaaacaaaa tatgcctttc ttggtttcca | 1260 |
| acaagcccca gtggtttttt cacatttatg acttcctgct cactggcctc atacgttcat | 1320 |
| tttcattgac cctgtggcac ttttttgtatt ctcattgggt cagactaaaa tcataggtaa | 1380 |
| tcaggttcaa aaaaaaaaaa aaaaaaaaa | 1410 |

<210> SEQ ID NO 5
<211> LENGTH: 2487
<212> TYPE: DNA
<213> ORGANISM: Mus musculus

<400> SEQUENCE: 5

| | |
|---|---:|
| aggactcgga gccacttcag cctgagcagt atgcttgaga ctgcagagct gtacttcaat | 60 |
| gtggaccatg gctacctgga gggcctggtt cgaggatgca agccagcct cctaactcag | 120 |
| caggactatg tcaacctagt gcagtgtgag accttggaag acctgaaaat tcatctccag | 180 |
| accacggact atggcaactt cctggctaat gaaacaaatc ctctcactgt ttccaaaatt | 240 |
| gacacggaga tgaggaagaa gctctgcaga gagtttgact atttccggaa tcattccttg | 300 |
| gagcccctga gcacatttct cacctacatg acatgcagct atatgataga caatataatt | 360 |
| ctacttatga atggggcctt gcaaaagaaa tctgtgaaag aagttctagc caagtgtcac | 420 |
| ccactgggcc gtttcacaga gatggaagct gtcaacattg cagagacccc ctcagatctc | 480 |
| ttcaaggctg tgctggttga acaccatta gctccattct ttcaagattg tatgtctgaa | 540 |
| aacactcttg atgaactgaa tattgaatta ctgcgcaata aactatacaa gtcttacctt | 600 |
| gaggcattct acaaattctg caaggatcac ggtgatgtca cagcagacgt tatgtgtccc | 660 |
| attcttgagt ttgaggccga cagacgcgct ttaatcatca ctctgaactc atttggcact | 720 |
| gaactaagca agaagacag ggagaccctc ttccccacct gcggcaggct ctatccagag | 780 |
| gggttgcggt tgttagctca agctgaagac tttgagcaga tgaagagagt ggcagataat | 840 |
| tatggagttt acaagccttt gtttgacgct gtcggtggca gtggggggaa gacactggaa | 900 |
| gacgttttct atgagagaga ggtacagatg aatgtgctgg cattcaacag gcaattccat | 960 |
| tatggtgtgt tttatgcgta tgtaaagttg aaggagcaag agatgagaaa tatcgtgtgg | 1020 |
| atagcagaat gcatctcaca gaggcatcga actaaaatca acagctacat tccaatttta | 1080 |
| taagccagtg tacagaagat catacatgtt gccatgaagt tattgaggaa aggaaggggg | 1140 |
| attgtgtcac attatctaga ttatataaaa gtaagtcata ccacctttcc ataaactaca | 1200 |
| tgtccactgg aagcccaagt aaacagaact tgaaacaaaa tatgcctttc ttggtttcca | 1260 |
| acaagcccca gtggtttttt cacatttatg acttcctgct cactggcctc atacgttcat | 1320 |
| tttcattgac cctgtggcac ttttttgtatt ctcattgggt cagactaaaa tcataggtaa | 1380 |
| tcaggttctt cacgagttct tttccgttct tctccccaag ctcaaacact gctttgcctt | 1440 |
| ttacgtgttt ggtccttcca tgcattcacg aaaatgcaaa gctggggta gctaacatac | 1500 |
| accatgcttg gtgaagacac gttcccttcc tttcccccaa gacttttgag aaagatagat | 1560 |
| tccccaaatg caagcattgt taaatttatt actaaattag attatcaacg cacacataga | 1620 |
| gacagagaga gagagagaga gacagacaga cagacagaca gaaggatgaa taacttatat | 1680 |

```
cgatatgtat accagtggtt ctgtcatact ttattccaga aaatccaact aattgtactt      1740
tattccttca gatagatgta gatacagcat ggttgctaca taaagttgaa acaatgcaga      1800
ggttgctcag aaaagaaaa atagcaaaat gtgtctccaa tctttctttt aaataggaaa      1860
tttttcttaa atatagtcta tgcttgctct gcttcacaaa ttaaatctgt gcagtcaaca      1920
tgatgactca gcaggtaaga gcttgaagtc aactccatga gttcgattcc tggaatctca      1980
catatggaag gagggaactg caaaactaca agatcatctt taatccttta atctttactt      2040 atgcaccca ccactacaca cacttacaaa agaattttaa agaagggcac agaaataatg      2100
tgaactaatt ttactataca ctctctatat acacatgcta tgtagaatag tatgcataaa      2160
ctaaggagca caacattttt atgtagaata atcatttata aatataacaa aaataatgtt      2220
ttgttgaact aagaagaaag ccaagtgcct actccttgac tgcagatgca atttacccag      2280
ctgcctcctg cccagaccaa cacaccttct caaccacctt agactgtcct ctcaaacct      2340 gacccaaaag aaaccttcc ctttctaaac tgttgtttca ggtattttgt ggcagcaaca      2400
caacaaagta actaatacag aaaactgata ctgccattgc tacaataaac ttgattttgg      2460
gattgccaaa aaaaaaaaaa aaaaaaa                                         2487

<210> SEQ ID NO 6
<211> LENGTH: 1306
<212> TYPE: DNA
<213> ORGANISM: Homo sapiens

<400> SEQUENCE: 6
ggaaactagt cacaaaaacc ctgactatca cctgatagat tgcttgtgct gcctgataat       60
tactcgcact tttcccaggc tagtgcaaat cttcaggggc cgtccaggac tacagagctg      120 tttcaccta ccttggcttc aatctcttcc cccatgctcg aaggtgcgga gctgtacttc      180
aacgtggacc atggctacct ggagggcctg gttcgaggat gcaaggccag cctcctgacc      240
cagcaagact atatcaacct ggtccagtgt gagaccctag aagacctgaa aattcatctc      300
cagactactg attatggtaa cttttttggct aatcacacaa atcctcttac tgtttccaaa      360
attgacactg agatgaggaa aagactatgt ggagaatttg agtatttccg gaatcattcc      420
ctggagcccc tcagcacatt tctcacctat atgacgtgca gttatatgat agacaatgtg      480
attctgctga tgaatggtgc attgcagaaa aaatctgtga agaaattct ggggaagtgc      540 caccccttgg gccgtttcac agaaatggaa gctgtcaaca ttgcagagac accttcagat      600
ctctttaatg ccattctgat cgaaacgcca ttagctccat tcttccaaga ctgcatgtct      660
gaaaatgctc tagatgaact gaatattgaa ttgctacgca ataaactata caagtcttac      720
cttgaggcat tctataaatt ctgtaagaat catggtgatg tcacagcaga agttatgtgt      780
cccattcttg agtttgaggc cgacagacgt gcttttatca tcactcttaa ctccttggc      840 actgaattga gcaaagaaga ccgagagacc ctctatccaa ccttcggcaa actctatcct      900 gagggggttgc ggctgttggc tcaagcagaa gactttgacc agatgaagaa cgtagcggat      960
cattacggag tatacaaacc tttatttgaa gctgtaggtg gcagtggggg aaagacattg     1020
gaggacgtgt tttacgagcg tgaggtacaa atgaatgtgc tggcattcaa cagacagttc     1080
cactacggtg tgttttatgc atatgtaaag ctgaaggaac aggaaattag aaatattgtg     1140
tggatagcag aatgtatttc acagaggcat cgaactaaaa tcaacagtta cattccaatt     1200
ttataaccca agtaaggttc tcaaatgtag aaaattataa atgttaaaag gaagttattg     1260
```

-continued

| aagaaaataa aagaaattat gttatattaa aaaaaaaaaa aaaaaa | 1306 |

<210> SEQ ID NO 7
<211> LENGTH: 2481
<212> TYPE: DNA
<213> ORGANISM: Homo sapiens

<400> SEQUENCE: 7

| ggaaactagt cacaaaaacc ctgactatca cctgatagat tgcttgtgct gcctgataat | 60 |
| tactcgcact tttcccaggc tagtgcaaat cttcaggggc cgtccaggac tacagagctg | 120 |
| tttcacccta ccttggcttc aatctcttcc cccatgctcg aaggtgcgga gctgtacttc | 180 |
| aacgtggacc atggctacct ggagggcctg gttcgaggat gcaaggccag cctcctgacc | 240 |
| cagcaagact atatcaacct ggtccagtgt gagaccctag aagacctgaa aattcatctc | 300 |
| cagactactg attatggtaa cttttttggct aatcacacaa atcctcttac tgtttccaaa | 360 |
| attgacactg agatgaggaa aagactatgt ggagaatttg agtatttccg gaatcattcc | 420 |
| ctggagcccc tcagcacatt tctcacctat atgacgtgca gttatatgat agacaatgtg | 480 |
| attctgctga tgaatggtgc attgcagaaa aatctgtga agaaattct ggggaagtgc | 540 |
| cacccccttgg gccgtttcac agaaatggaa gctgtcaaca ttgcagagac accttcagat | 600 |
| ctctttaatg ccattctgat cgaaacgcca ttagctccat tcttccaaga ctgcatgtct | 660 |
| gaaaatgctc tagatgaact gaatattgaa ttgctacgca ataaactata caagtcttac | 720 |
| cttgaggcat tctataaatt ctgtaagaat catggtgatg tcacagcaga agttatgtgt | 780 |
| cccattcttg agtttgaggc cgacagacgt gcttttatca tcactcttaa ctcctttggc | 840 |
| actgaattga gcaaagaaga ccgagagacc ctctatccaa ccttcggcaa actctatcct | 900 |
| gagggggttgc ggctgttggc tcaagcagaa gactttgacc agatgaagaa cgtagcggat | 960 |
| cattacggag tatacaaacc tttatttgaa gctgtaggtg gcagtggggg aaagacattg | 1020 |
| gaggacgtgt tttacgagcg tgaggtacaa atgaatgtgc tggcattcaa cagacagttc | 1080 |
| cactacggtg tgttttatgc atatgtaaag ctgaaggaac aggaaattag aaatattgtg | 1140 |
| tggatagcag aatgtatttc acagaggcat cgaactaaaa tcaacagtta cattccaatt | 1200 |
| ttataaccca gtaaggttc tcaaatgtag aaaattataa atgttaaaag gaagttattg | 1260 |
| aagaaaataa aagaaattat gttatattat ctagactaca caaaagtaag ccacactata | 1320 |
| tcttcatgag ttgcaaatcc atggaaacac agtaaaccag ccctgaaaca aagcatttcc | 1380 |
| ttgttttcag tggtattaga tcttgtttcc acatgtctgt ctcattcttc actgggcctt | 1440 |
| acaggttagt tttaattaac tctatggtat ttttcttatt cttgtttgat catgttaaaa | 1500 |
| attggaccta ataaaagtat tttattcttg cttttccatg cttctctaca ggtccaaata | 1560 |
| ctgaatgtct cctttacttt ttctctttta aattttttttc tagacagggt ctcactctgt | 1620 |
| cacctaggct acagtgcagt ggtgtgatca cagctcactg cagcctcgac ttcccaggct | 1680 |
| caagtgatcc tcccagctct cagcctccaa agtagctggc actacaagtg tacacccca | 1740 |
| cacaaggcta gttttgtat tttttgtaga gacagggttt caacatatta tccaggctgg | 1800 |
| tgtcgaattc ctgggctcca gggatccaca gtccccttg gcctcccaaa gtgttgggat | 1860 |
| tacatgcatg agccactgtg ctgggcttca tttacatttt aactgtctgt tccttgccta | 1920 |
| gattcacaga aatccaaagc tgtatgtagt caacatggtt cacaagtgtt ggaaaatgtg | 1980 |
| ttttttgttt tgttttgttt tgtttcgttt tgttttgaga cagagtttcc ctctgtcgcc | 2040 |
| caggctagag tgcaatggcg tgatctcggc tcactgcaac ctccacctcc cagattcaag | 2100 |

-continued

| | | | | |
|---|---|---|---|---|
| caactctctg | cctcagcctc | ccgagtagct | gggattacaa | gcacccacca ctacactcag | 2160 |
| ctaattttt | gtatttttag | tagagccggg | gtttcaccat | cttggccagg ctgatcttga | 2220 |
| actcctgagc | tcatgatcca | cccgcctcag | cctcccaaag | tgctgggatt acaggcccct | 2280 |
| tgttcagcca | ctgcacctgg | cccttattt | tgtttttgtt | ttctaatata ctttgatgta | 2340 |
| atcagcttga | gaaagcaaca | caatttcaaa | tcctatcttc | tagatgcaag cagtgttaaa | 2400 |
| tttgttaata | aatttgcttt | tcacaccttt | ctttaaataa | aaggtatatc tctctttaaa | 2460 |
| aaaaaaaaaa | aaaaaaaaaa | a | | | 2481 |

<210> SEQ ID NO 8
<211> LENGTH: 4251
<212> TYPE: DNA
<213> ORGANISM: Mus musculus

<400> SEQUENCE: 8

| | | | | | |
|---|---|---|---|---|---|
| ctaaaccacg | cggagggccg | ttccagcaca | gctggggaaa | acaggccggg ccaggcttgc | 60 |
| gggagagttg | gatatgttta | gtatctagag | gacgtttgtt | tttcagaact cctctctccc | 120 |
| ttccgaaatc | tggcaggcgt | tagtcatccg | ctgctcagca | cgaaccctca agtgtgcttg | 180 |
| tgtggctcgt | cgggcttcct | cccggcgccc | cgccctcggg | ctcgcacgag cagaccggtc | 240 |
| agcgcccact | cccaccccc | aggcctgagg | tgccggcgg | cctgccgctc ccccgggtgc | 300 |
| ttagcatccc | gggctgcaga | ggctcgcccc | gcgcggcgcg | gcgccaggtt ggggcaggga | 360 |
| agaaagttat | aaagtgccgc | gaggagttgg | gcggtccgag | gaagagaggc ggaagaggag | 420 |
| gactcggctg | agttcccgcg | gcgatcgtgg | ggtccgcggg | tgcctgtccc gcagctcacc | 480 |
| accgcagcta | gacgccagcc | tttctgctcc | cgggtgggcg | ccggagactc agcgggaggc | 540 |
| gaggaacttg | tcccgagagc | tgtcgctgcg | ggcctcattg | tctgcagcaa ctctccggaa | 600 |
| tccggagtgg | gagaactgga | ctctgtccac | tgggatttgc | ccagagttcc ggcggcagct | 660 |
| gtggcggctg | cggagactct | ctttgtcctc | ccaggacctc | gctctctctc ctcagtggca | 720 |
| gctgttgggt | ggctctgagc | ttggagaggg | catcccagcc | ccgctcagcc tctgaccccc | 780 |
| gggcgagtcc | ccggtgactc | cgcctctttc | acgtctctgc | tctgtgaagc ccggagccca | 840 |
| gaaccccgag | cccaagggac | tgtgagccag | agagagctgc | cgggcccgg ccacaggatg | 900 |
| gtggccggtc | ggtcccgggc | gcgcagccct | gggagctggc | tgttccctgg cctgtggttg | 960 |
| ttggctgtgg | gcggtccggg | gtcgttgctg | caagcccagg | agcagccctc ttgcaaaaaa | 1020 |
| gccttcgatt | tgtacttcgt | actggacaag | tctggcagtg | tagcaaataa ctggattgaa | 1080 |
| atttataatt | ttgtccacca | gctgacagag | agatttgtga | gccctgaaat gagattgtcc | 1140 |
| ttcattgtgt | tttcttccca | agcaaccatt | attttgccat | taactggaga caggtacaaa | 1200 |
| attggcaaag | gactggagga | tttaaaggcc | gttaagccag | ttggagaaac atacatccat | 1260 |
| gaaggactaa | agcttgcaaa | cgaacaaatt | caaaatgcag | gaggcttaaa agcctccagt | 1320 |
| atcataattg | ctttgacgga | cggtaagctg | gacggcctgg | taccatctta tgcagagaac | 1380 |
| gaggcaaaga | agtccaggtc | acttggcgct | agtgtttact | gcgttggggt ccttgatttt | 1440 |
| gaacaagctc | agctgaaaag | aattgctgat | tccaaggacc | aggttttccc tgtcaaaggt | 1500 |
| ggatttcaag | ctctcaaagg | catcatcaac | tctatattag | ctcaatcatg tactgaaatc | 1560 |
| ctggaattga | gtccttcaag | tgtctgtgta | ggggagaaat | ttcaagttgt tctgactgga | 1620 |
| agagcagtca | cgtcgatcag | tcacgatggc | agtgtcctct | gtacattcac tgcaaacagc | 1680 |

-continued

```
acatatacaa agagtgagaa gccagtgagc attcagccaa gttccatcct ttgtcctgca    1740
cctgtcctga acaaagatgg agaaactctt gaagtttcaa tcagctataa tgatgggaag    1800
tctgctgtct caagatcctt aacaatcaca gccacagaat gtaccaatgg gattgcagcc    1860
atcgtagcta ttttggtgtt gttgctgctc ttgggtgctg ccttgatgtg gtggttttgg    1920
cccctttgct gcaaagtggt tatcaaggac cctcccccac caccttctgc accaatggag    1980
gaggaggagg aggatccttt gcccaacaag aagtggccga ctgtggacgc ttcctactac    2040
ggaggtcgag gtgttggagg aattaaaagg atggaggtcc gctggggaga taaaggatct    2100
acagaggaag gtgcaaggct agagaaagca aaaaatgctg tggtgatggt ccctgaagaa    2160
gagatcccca tcccatccag accacctcga cccagaccca cacaccaggc acctcagaca    2220
aagtggtaca cgccaatcaa gggtcgtttg gatgcactct gggctttgat catgaagcag    2280
tatgaccggg tgtccttgat gagaccccag gaaggtgatg agggccgatg cataaacttc    2340
tcccgggttc acatcaata agacgggaga acaaagaatg agaagataag aagacagtgt    2400
gacagtgtat cttcatgatg ctgatttcca acagaaccga cagtccggtg catctcagaa    2460
gttcttggga acacagccca ttttctctct gtcaggaaat gtttcctctg ccttctgctt    2520
tctgtgcact aaacattttc caacacttgt tctgccatcg acatgagagg tgatgaaagt    2580
catcggcgat agcccatgat tcacgacact gaaaatcccg aggaatgtta gtttgcatgc    2640
tagggtttat gcaaagctcg ttttgactat gtaagaggac aaagcagaca catcgatgat    2700
gtaatgatac caaagctagg actgcaaatc catcagccac agaggtttgc aatggagact    2760
ggtgattctg ccatgaatgt gtggcccctg tgcttttgtt tggcaagatc tttagctaca    2820
agcaaaacat gaagtttcct cccaggctaa acagataatg gagtccactg ccttgtagct    2880
atgtcagata gcaaagcctt tccaagtcct ccattacttt gtgccttaca ggaaatttct    2940
gactagaaaa tcttgtcatt gttacactga aagtgcacac gcatgacaaa atgtagacga    3000
gacgcctcaa ggtactggat gcaagcagga ttttttgccct ttagttttcc aagacacctt    3060
tctttcatta tgcacttgag acaagagaat taatagagcg ttaattcaac aggaagaccg    3120
cctccaacca aagacctgga gcgcagcata aggacttgtg atttgagacg ttgtccccag    3180
cctggtagat ccccctttct cagcatttgg gatttagcag tgcataaagc attaatatct    3240
gtaaaaacac ctagatgttt gtttggcttt taatttaagg aagctgcaac cacaaagctt    3300
ccgctcaggg ttttttcttc cttcaagtct ccaagggctc ttcagcgtca caagccagca    3360
actctctttg catgaaaatt tcaaagttta attaatataa ttaaaggcaa cagcaagcag    3420
cagcctgtga agattttgct catctttttt atgccttttg acattgagtg acctatcact    3480
gtatgcatgt tacttagaaa ttgaggagca ccacaccttg ttgtggttc agcctgggaa    3540 agagacctcc ttccttctgt ttataaatta aaatcaggag gggcgccatc agaaagcatg    3600
gacaatatac atactataaa ttttttagaaa tatcaccatc gtgtcacgtc aacgatgcca    3660
aattatgtta gtgtgagcag aaacccggtg ggggaggaag gcggcagcag ccgaaggaaa    3720
tagctcagat aatctagtca ctttcgatac tgtacttcag atgcgaaatg gatattcgac    3780
tggaaacctg acaaagcgcg cctgctttga tgtgaactgt tatagacaat gaccagtggc    3840
cgggtcagtg ggatgtctct ctgcgagcac aaaggcttat caaatgacac taaaaataag    3900
ttcaacaacc atcactttgg aagggagaag gcgaacattt catgtttggc gggcatgtga    3960
gtgcaggaga tggaaagagc catttagagc atcctacata aattgcccgc attgtactct    4020
tcatggaaat ttcaaaggac ggcagtgata tttttcattg gtgtccacgt ttgtggcact    4080
```

```
gctccaagaa gccttatgca cacatacaaa tatacaaatg cacacaccta cactctctag    4140
ctttaatctt tttgctcaac cttatttata tcactgactg gctggatcca aagtcacacc    4200
tccacatatt agtgaataaa aaattttac ctgttaaaaa aaaaaaaaa a              4251
```

<210> SEQ ID NO 9
<211> LENGTH: 4081
<212> TYPE: DNA
<213> ORGANISM: Homo sapiens

<400> SEQUENCE: 9

```
gatttgtctg gttaattccg ataacgaacg agactctggc atgctaacta gttacgcgac      60
ccccgagcgg tcggcgtccc ccaacttctt agagggacaa gtggcgttca gccacccgag     120
attgagcaat aacaggtctg tgatgccctt agatgtccgg ggctgcacgc gcagtgccag     180
agtccagcac cggaggaaaa gtttcggagt gcggagggag ttggggccgc cggaggagaa     240
gagtctccac tcctagtttg ttctgccgtc gccgcgtccc aggaccccct tgtcccgaag     300
cgcacggcag cggggggggac ttcagccctc caggcggggt gggttccagg tccgggtccg     360
aggcgggcgc tggaggctcg gccccaggcc ggagaggaac tcctttcgcg agctgtcgcc     420
gtgggcccgc attgtctgca ggaactctcc ggaatcggga gggggaggac tggatcgcgc     480
ttccactggg attcgtcaag agttccggcg gcagctgcgg cggtggcgga gactcccttt     540
gtcctctcag gacctccctc tctccctccc tgtcagctgg tgggtcccgc tgccgcaggc     600
gccggcgtct cagctgctcg ccgcccccca ccccagagtg cgtgccgggt gactcccgcc     660
acctttgcga ccctcctgag cttagggac tgcgagcggg agggagtctc aggcccccgg     720
ccgcaggatg gtggcggagc ggtccccggc ccgcagcccc gggagctggc tgttccccgg     780
gctgtggctg ttggtgctca gcggtcccgg ggggctgctg cgcgcccagg agcagccctc     840
ctgcagaaga gcctttgatc tctacttcgt cctggacaag tctgggagtg tggcaaataa     900
ctggattgaa atttataatt cgtacagca acttgcggag agatttgtga gccctgaaat     960
gagattatct ttcattgtgt tttcttctca agcaactatt attttgccat taactggaga    1020
cagaggcaaa atcagtaaag gcttggagga tttaaaacgt gttagtccag taggagagac    1080
atatatccat gaaggactaa agctagcgaa tgaacaaatt cagaaagcag gaggcttgaa    1140
aacctccagt atcataattg ctctgacaga tggcaagttg gacggtctgg tgccatcata    1200
tgcagagaaa gaggcaaaga tatccaggtc acttgggct agtgtttatt gtgttggtgt    1260
ccttgatttt gaacaagcac agcttgaaag aattgctgat tccaaggagc aagttttccc    1320
tgtcaaaggt ggatttcagg ctcttaaagg aataattaat tctatactag ctcagtcatg    1380
tactgaaatc ctagaattgc agccctcaag tgtctgtgtg ggggaggaat tcagattgt    1440
cttaagtgga agaggattca tgctgggcag tcggaatggc agtgttctct gcacttacac    1500
tgtaaatgaa acatatacaa cgagtgtaaa accagtaagt gtacagctta attctatgct    1560
ttgtcctgca cctatcctga ataaagctgg agaaactctt gatgtttcag tgagctttaa    1620
tggaggaaaa tctgtcattt caggatcatt aattgtcaca gccacagaat gttctaacgg    1680
gatcgcagcc atcattgtta ttttggtgtt actgctactc ctggggatcg gtttgatgtg    1740
gtggttttgg ccccttttgct gcaaagtggt tattaaggat cctccaccac cacccgcccc    1800
tgcaccaaaa gaggaggaag aagaaccttt gcctactaaa aagtggccaa ctgtggatgc    1860
ttcctattat ggtggtcgag gggttggagg aattaaaaga atggaggttc gttggggtga    1920
```

-continued

```
taaaggatct actgaggaag gtgcaaggct agagaaagcc aaaaatgctg tggtgaagat    1980
tcctgaagaa acagaggaac ccatcaggcc tagaccacct cgacccaaac ccacacacca    2040
gcctcctcag acaaaatggt acaccccaat taagggtcgt cttgatgctc tctgggcttt    2100
gttgaggcgg cagtatgacc gggtttcttt gatgcgacct caggaaggag atgagggccg    2160
gtgcataaac ttctcccgag ttccatctca gtaaaaggga agcaggaaga ccaagaaggt    2220
acgaagatgg cacattttca catagctgat tttcaaccaa atgaaaaaaa tcaagtgcat    2280
ttcagaagct tttggaagag cagcttaatt cctctcagtc gggaaatgtt ttctctgcct    2340
tctgctttgc ttgcaccaaa catttctaaa cacttgttct gccatctaca tgggaggtga    2400
tgaaactcag tggtaactca tgatttatga cattgaaaat aaagaggaac attgacctgc    2460
agactatggt ttgtacaaga aagtttgttt gaatgtgtag aagaggaaaa agcaacaaca    2520
gcaacaacac gaagatgata ccaaaacaag gaccacaaaa caactagcca tgatgggaga    2580
caggagtttt ttacatggaa acatggcact tgtgttttta tgtggcaaga tctttatcca    2640
taggcagagt atgaaatttc ccaccaggct aagcaaataa agaagtccat tgccttatag    2700
ctatgtcaga tcacagaatc cttccaagtg ctctatcaca gtgtgcctta tgggaagttt    2760
ctgactggaa atcttgtca ttctaacact gaaaagtgca cacgcatgac aaaatgtaga    2820
caagatgcct caaggtattg gtagcaagca agattttgcc ctttagtttt cgaagacacc    2880
tttctttcat tatgcactcg ggacaagaaa attaatagag cgttattcca cagaaggcct    2940
ctagccagag atcttgagtg tagtgcaagg gactcatgct ttgcgaactt gtccctgtga    3000
ctagtagatt ccccctttc ctgtgtttag gatttagtag tgcataaagc attaatatcc    3060
ataaacatac ctagaagttt gttttgcttt taatttaaag gaagcagtaa ccacaaagct    3120
tccgctcagg gttttttctt tcttcaagtc tccaagggct cttcagcgtc acaagccagc    3180
aactctcttt gcattaaaat ttcaaagttt aattaatata attaaaagca acagcaagca    3240
gcagcctgtg aagattttgc tcatcttttt tatgcctttt gacattgaat gaccctattac    3300
tgtatgcgca ttacttggat tttgaggggc actctacctt ggttatgatt cagtagagga    3360
aaaagaccac ctttcttcaa tttacaaatt aaatcttctg gagggtcgct atcacaaaac    3420
cattgacgat gtatgtatta aattttttta gaaaaaccac catcgtgtca cgtcgacgat    3480
gcccaaatta tgttagcgtg agcagaaaca ccgtggggga ggaaggcagc agctgaagaa    3540
aaaagctcaa atgatctagt cactttcgat actgtacttc agatgcgaaa tggatattcg    3600
agtggaaacc tgacaaagtg cgcctgcttt gatgtgaact ggtatagaca atgaccagtg    3660
gctgggtcag tgggatgtct ctctgtgagc acaaaggctt atcaaatgac actaaaaata    3720
agttcaacaa ccatcacatt ggaagggaga aggcgaacat tcatgtttg gcgggcatgt    3780
gagtgcacaa gatggaaaga gcgattggag catcctggta taattacccc cattgtgctc    3840
ttaatggaaa tttcaaagga cgggagtatt ctgttggttg gtgtccaggt ttgtggcact    3900
gttccaagag gccttacaca cacacacaaa tatataattt tctatacata tatatcctct    3960
agcttgaaac ttttgctcaa gtttatttat gtcactggct ggctggatcc aaagtcatgt    4020
gtccacacat tcataaataa aaattttacc tataaaaaaa aaaaaaaaaa aaaaaaaaa     4080
a                                                                   4081
```

<210> SEQ ID NO 10
<211> LENGTH: 547
<212> TYPE: PRT
<213> ORGANISM: Mus musculus

<400> SEQUENCE: 10

```
Met Glu Asp Glu Asp Lys Thr Ala Glu Cys Gln His Ser Lys Pro Pro
1               5                   10                  15
Thr Gly Ile Thr His Glu Ala Pro Pro His His Glu Leu Gln Glu Glu
            20                  25                  30
Arg Val Met Ser Leu Arg Gly Thr Asp Arg Ser Glu Pro Thr Glu Gly
        35                  40                  45
Ser Asn Leu Leu Thr Ser Gly Glu Lys Lys Pro Gln Asp Ser Pro Thr
50                  55                  60
Glu Pro Asn Gly Leu Gln Ser Leu Arg Arg Phe Leu Ala Cys Pro Pro
65                  70                  75                  80
Arg Gly Cys Leu Ala Arg Val Ile Thr Asn Gly Thr Met Val Val Leu
                85                  90                  95
Leu Trp Ala Met Val Trp Ser Val Thr Gly Pro Glu Cys Leu Pro Gly
            100                 105                 110
Gly Asn Leu Phe Gly Ile Ile Ile Leu Phe Tyr Cys Ser Ile Thr Gly
        115                 120                 125
Gly Lys Leu Phe Gly Leu Ile Lys Phe Pro Thr Leu Pro Pro Leu Pro
130                 135                 140
Pro Leu Leu Gly Met Leu Leu Ala Gly Phe Leu Leu Arg Asn Ile Pro
145                 150                 155                 160
Val Ile Asn Asp Ser Val Arg Ile Gln His Lys Trp Ser Ser Ser Leu
                165                 170                 175
Arg Ser Ile Ala Leu Ser Val Ile Leu Val Arg Ala Gly Leu Gly Leu
            180                 185                 190
Asp Ser Lys Ala Leu Arg Lys Leu Lys Gly Val Cys Val Arg Leu Ala
        195                 200                 205
Met Gly Pro Cys Ile Val Glu Ala Cys Ala Ser Ala Ile Leu Ser His
210                 215                 220
Phe Leu Met Gly Leu Pro Trp Gln Trp Gly Phe Ile Leu Gly Phe Val
225                 230                 235                 240
Val Gly Ala Val Ser Pro Ala Val Val Pro Ser Met Leu Leu Leu
                245                 250                 255
Gln Glu Gly Gly Tyr Gly Val Gly Lys Gly Ile Pro Thr Leu Leu Met
            260                 265                 270
Ala Ala Gly Ser Phe Asp Asp Ile Leu Ala Ile Thr Gly Phe Asn Thr
        275                 280                 285
Cys Leu Gly Val Ala Phe Ser Thr Gly Ser Thr Val Phe Asn Ile Phe
290                 295                 300
Arg Gly Ile Leu Glu Val Val Ile Gly Val Ala Ala Gly Ser Phe Leu
305                 310                 315                 320
Gly Phe Phe Ile Gln Tyr Phe Pro Ser Arg Asp Gln Asp Asn Leu Val
                325                 330                 335
Trp Lys Arg Ala Phe Leu Val Leu Gly Phe Ala Val Leu Ala Val Phe
            340                 345                 350
Ser Ser Val Tyr Phe Ser Phe Pro Gly Ser Gly Leu Cys Thr Leu
        355                 360                 365
Val Met Ala Phe Leu Ala Gly Met Arg Trp Thr Asp Lys Lys Ser Glu
370                 375                 380
Val Glu Lys Val Ile Ala Val Thr Trp Asp Val Phe Gln Pro Leu Leu
385                 390                 395                 400
Phe Gly Leu Ile Gly Ala Glu Val Ser Ile Val Ser Leu Arg Ala Glu
```

```
                    405                 410                 415
Thr Val Gly Leu Cys Val Ala Thr Leu Ser Ile Ala Val Leu Ile Arg
            420                 425                 430

Ile Leu Thr Thr Phe Leu Met Val Cys Phe Ala Gly Phe Asn Ile Lys
        435                 440                 445

Glu Lys Ile Phe Ile Ser Phe Ala Trp Leu Pro Lys Ala Thr Val Gln
    450                 455                 460

Ala Ala Ile Gly Ser Val Ala Leu Asp Thr Ala Arg Ser His Gly Glu
465                 470                 475                 480

Lys Gln Leu Glu Asp Tyr Gly Met Asp Val Leu Thr Val Ala Phe Leu
                485                 490                 495

Ala Ile Leu Ile Thr Ala Pro Ile Gly Ser Leu Leu Ile Gly Leu Leu
            500                 505                 510

Gly Pro Arg Val Leu Gln Lys Ser Glu His Arg Thr Glu Glu Glu Val
        515                 520                 525

Gln Gly Glu Thr Ser Ala His Ile Gln Arg Lys Pro Glu Asp Ser Ile
    530                 535                 540

Thr Glu Ala
545

<210> SEQ ID NO 11
<211> LENGTH: 538
<212> TYPE: PRT
<213> ORGANISM: Homo sapiens

<400> SEQUENCE: 11

Met Gly Asp Glu Asp Lys Arg Ile Thr Tyr Glu Asp Ser Glu Pro Ser
1               5                   10                  15

Thr Gly Met Asn Tyr Thr Pro Ser Met His Gln Glu Ala Gln Glu Glu
            20                  25                  30

Thr Val Met Lys Leu Lys Gly Ile Asp Ala Asn Glu Pro Thr Glu Gly
        35                  40                  45

Ser Ile Leu Leu Lys Ser Ser Glu Lys Lys Leu Gln Glu Thr Pro Thr
    50                  55                  60

Glu Ala Asn His Val Gln Arg Leu Arg Gln Met Leu Ala Cys Pro Pro
65                  70                  75                  80

His Gly Leu Leu Asp Arg Val Ile Thr Asn Val Thr Ile Ile Val Leu
                85                  90                  95

Leu Trp Ala Val Val Trp Ser Ile Thr Gly Ser Glu Cys Leu Pro Gly
            100                 105                 110

Gly Asn Leu Phe Gly Ile Ile Ile Leu Phe Tyr Cys Ala Ile Ile Gly
        115                 120                 125

Gly Lys Leu Trp Gly Leu Leu Ser Tyr Leu His Cys Leu His Cys Leu
    130                 135                 140

Leu Phe Leu Gly Met Leu Leu Ala Gly Phe Leu Ile Arg Asn Ile Pro
145                 150                 155                 160

Val Ile Asn Asp Asn Val Gln Ile Lys His Lys Trp Ser Ser Ser Leu
                165                 170                 175

Arg Ser Ile Ala Leu Ser Ile Leu Val Arg Ala Gly Leu Gly Leu
            180                 185                 190

Asp Ser Lys Ala Leu Lys Lys Leu Lys Gly Val Cys Val Arg Leu Ser
        195                 200                 205

Met Gly Pro Cys Ile Val Glu Ala Cys Thr Ser Ala Leu Leu Ala His
    210                 215                 220
```

-continued

```
Tyr Leu Leu Gly Leu Pro Trp Gln Trp Gly Phe Ile Leu Gly Phe Val
225                 230                 235                 240

Leu Gly Ala Val Ser Pro Ala Val Val Pro Ser Met Leu Leu Leu
        245                 250                 255

Gln Gly Gly Gly Tyr Gly Val Glu Lys Gly Val Pro Thr Leu Leu Met
            260                 265                 270

Ala Ala Gly Ser Phe Asp Asp Ile Leu Ala Ile Thr Gly Phe Asn Thr
        275                 280                 285

Cys Leu Gly Ile Ala Phe Ser Thr Gly Ser Thr Val Phe Asn Val Leu
    290                 295                 300

Arg Gly Val Leu Glu Val Ile Gly Val Ala Thr Gly Ser Val Leu
305                 310                 315                 320

Gly Phe Phe Ile Gln Tyr Phe Pro Ser Arg Asp Gln Asp Lys Leu Val
                325                 330                 335

Cys Lys Arg Thr Phe Leu Val Leu Gly Leu Ser Val Leu Ala Val Phe
            340                 345                 350

Ser Ser Val His Phe Gly Phe Pro Gly Ser Gly Gly Leu Cys Thr Leu
        355                 360                 365

Val Met Ala Phe Leu Ala Gly Met Gly Trp Thr Asp Arg Glu Lys Ala
    370                 375                 380

Glu Val Glu Lys Ile Ile Ala Val Ala Trp Asp Ile Phe Gln Pro Leu
385                 390                 395                 400

Leu Phe Gly Leu Ile Gly Ala Glu Val Ser Ile Ala Ser Leu Arg Pro
                405                 410                 415

Glu Thr Val Gly Leu Cys Val Ala Thr Val Gly Ile Ala Val Leu Ile
            420                 425                 430

Arg Ile Leu Thr Thr Phe Leu Met Val Cys Phe Ala Gly Phe Asn Leu
        435                 440                 445

Lys Glu Lys Ile Phe Ile Ser Phe Ala Trp Leu Pro Lys Ala Thr Val
    450                 455                 460

Gln Ala Ala Ile Gly Ser Val Ala Leu Asp Thr Ala Arg Ser His Gly
465                 470                 475                 480

Glu Lys Gln Leu Glu Asp Tyr Gly Met Asp Val Leu Thr Val Ala Phe
                485                 490                 495

Leu Ser Ile Leu Ile Thr Ala Pro Ile Gly Ser Leu Leu Ile Gly Leu
            500                 505                 510

Leu Gly Pro Arg Leu Leu Gln Lys Val Glu His Gln Asn Lys Asp Glu
        515                 520                 525

Glu Val Gln Gly Glu Thr Ser Val Gln Val
    530                 535
```

```
<210> SEQ ID NO 12
<211> LENGTH: 238
<212> TYPE: PRT
<213> ORGANISM: Homo sapiens

<400> SEQUENCE: 12

Met Gly Asp Glu Asp Lys Arg Ile Thr Tyr Glu Asp Ser Glu Pro Ser
1               5                   10                  15

Thr Gly Met Asn Tyr Thr Pro Ser Met His Gln Glu Ala Gln Glu Glu
            20                  25                  30

Thr Val Met Lys Leu Lys Gly Ile Asp Ala Asn Glu Pro Thr Glu Gly
        35                  40                  45

Ser Ile Leu Leu Lys Ser Ser Glu Lys Lys Leu Gln Glu Thr Pro Thr
    50                  55                  60
```

-continued

```
Glu Ala Asn His Val Gln Arg Leu Arg Gln Met Leu Ala Cys Pro Pro
 65                  70                  75                  80

His Gly Leu Leu Asp Arg Val Ile Thr Asn Val Thr Ile Ile Val Leu
                 85                  90                  95

Leu Trp Ala Val Val Trp Ser Ile Thr Gly Ser Glu Cys Leu Pro Gly
                100                 105                 110

Gly Asn Leu Phe Gly Ile Ile Ile Leu Phe Tyr Cys Ala Ile Ile Gly
            115                 120                 125

Gly Lys Leu Trp Gly Leu Leu Ser Tyr Leu His Cys Leu His Cys Leu
        130                 135                 140

Leu Phe Leu Gly Met Leu Leu Ala Gly Phe Leu Ile Arg Asn Ile Pro
145                 150                 155                 160

Val Ile Asn Asp Asn Val Gln Ile Lys His Lys Trp Ser Ser Ser Leu
                165                 170                 175

Arg Ser Ile Ala Leu Ser Ile Ile Leu Val Arg Ala Gly Leu Gly Leu
            180                 185                 190

Asp Ser Lys Ala Leu Lys Lys Leu Lys Gly Val Cys Val Arg Leu Ser
        195                 200                 205

Met Gly Pro Cys Ile Val Glu Ala Cys Thr Ser Ala Leu Leu Ala His
    210                 215                 220

Tyr Leu Gly Leu Pro Trp Gln Trp Gly Phe Ile Leu Gly
225                 230                 235

<210> SEQ ID NO 13
<211> LENGTH: 350
<212> TYPE: PRT
<213> ORGANISM: Mus musculus

<400> SEQUENCE: 13

Met Leu Glu Thr Ala Glu Leu Tyr Phe Asn Val Asp His Gly Tyr Leu
  1               5                  10                  15
Glu Gly Leu Val Arg Gly Cys Lys Ala Ser Leu Leu Thr Gln Gln Asp
                 20                  25                  30
Tyr Val Asn Leu Val Gln Cys Glu Thr Leu Glu Asp Leu Lys Ile His
             35                  40                  45
Leu Gln Thr Thr Asp Tyr Gly Asn Phe Leu Ala Asn Glu Thr Asn Pro
 50                  55                  60
Leu Thr Val Ser Lys Ile Asp Thr Glu Met Arg Lys Lys Leu Cys Arg
 65                  70                  75                  80
Glu Phe Asp Tyr Phe Arg Asn His Ser Leu Glu Pro Leu Ser Thr Phe
                 85                  90                  95
Leu Thr Tyr Met Thr Cys Ser Tyr Met Ile Asp Asn Ile Ile Leu Leu
            100                 105                 110
Met Asn Gly Ala Leu Gln Lys Lys Ser Val Lys Glu Val Leu Ala Lys
        115                 120                 125
Cys His Pro Leu Gly Arg Phe Thr Glu Met Glu Ala Val Asn Ile Ala
    130                 135                 140
Glu Thr Pro Ser Asp Leu Phe Lys Ala Val Leu Val Glu Thr Pro Leu
145                 150                 155                 160
Ala Pro Phe Phe Gln Asp Cys Met Ser Glu Asn Thr Leu Asp Glu Leu
                165                 170                 175

Asn Ile Glu Leu Leu Arg Asn Lys Leu Tyr Lys Ser Tyr Leu Glu Ala
            180                 185                 190

Phe Tyr Lys Phe Cys Lys Asp His Gly Asp Val Thr Ala Asp Val Met
        195                 200                 205

Cys Pro Ile Leu Glu Phe Glu Ala Asp Arg Arg Ala Leu Ile Ile Thr
    210                 215                 220

Leu Asn Ser Phe Gly Thr Glu Leu Ser Lys Glu Asp Arg Glu Thr Leu
225                 230                 235                 240

Phe Pro Thr Cys Gly Arg Leu Tyr Pro Glu Gly Leu Arg Leu Leu Ala
                245                 250                 255
```

```
Gln Ala Glu Asp Phe Glu Gln Met Lys Arg Val Ala Asp Asn Tyr Gly
            260                 265                 270

Val Tyr Lys Pro Leu Phe Asp Ala Val Gly Ser Gly Gly Lys Thr
        275                 280                 285

Leu Glu Asp Val Phe Tyr Glu Arg Glu Val Gln Met Asn Val Leu Ala
        290                 295                 300

Phe Asn Arg Gln Phe His Tyr Gly Val Phe Tyr Ala Tyr Val Lys Leu
305                 310                 315                 320

Lys Glu Gln Glu Met Arg Asn Ile Val Trp Ile Ala Glu Cys Ile Ser
                325                 330                 335

Gln Arg His Arg Thr Lys Ile Asn Ser Tyr Ile Pro Ile Leu
            340                 345                 350

<210> SEQ ID NO 14
<211> LENGTH: 350
<212> TYPE: PRT
<213> ORGANISM: Homo sapiens

<400> SEQUENCE: 14

Met Leu Glu Gly Ala Glu Leu Tyr Phe Asn Val Asp His Gly Tyr Leu
1               5                   10                  15

Glu Gly Leu Val Arg Gly Cys Lys Ala Ser Leu Leu Thr Gln Gln Asp
            20                  25                  30

Tyr Ile Asn Leu Val Gln Cys Glu Thr Leu Glu Asp Leu Lys Ile His
        35                  40                  45

Leu Gln Thr Thr Asp Tyr Gly Asn Phe Leu Ala Asn His Thr Asn Pro
    50                  55                  60

Leu Thr Val Ser Lys Ile Asp Thr Glu Met Arg Lys Arg Leu Cys Gly
65                  70                  75                  80

Glu Phe Glu Tyr Phe Arg Asn His Ser Leu Glu Pro Leu Ser Thr Phe
                85                  90                  95

Leu Thr Tyr Met Thr Cys Ser Tyr Met Ile Asp Asn Val Ile Leu Leu
            100                 105                 110

Met Asn Gly Ala Leu Gln Lys Lys Ser Val Lys Glu Ile Leu Gly Lys
        115                 120                 125

Cys His Pro Leu Gly Arg Phe Thr Glu Met Glu Ala Val Asn Ile Ala
    130                 135                 140

Glu Thr Pro Ser Asp Leu Phe Asn Ala Ile Leu Ile Glu Thr Pro Leu
145                 150                 155                 160

Ala Pro Phe Phe Gln Asp Cys Met Ser Glu Asn Ala Leu Asp Glu Leu
                165                 170                 175

Asn Ile Glu Leu Leu Arg Asn Lys Leu Tyr Lys Ser Tyr Leu Glu Ala
            180                 185                 190

Phe Tyr Lys Phe Cys Lys Asn His Gly Asp Val Thr Ala Glu Val Met
        195                 200                 205

Cys Pro Ile Leu Glu Phe Glu Ala Asp Arg Arg Ala Phe Ile Ile Thr
    210                 215                 220

Leu Asn Ser Phe Gly Thr Glu Leu Ser Lys Glu Asp Arg Glu Thr Leu
225                 230                 235                 240

Tyr Pro Thr Phe Gly Lys Leu Tyr Pro Glu Gly Leu Arg Leu Leu Ala
                245                 250                 255

Gln Ala Glu Asp Phe Asp Gln Met Lys Asn Val Ala Asp His Tyr Gly
            260                 265                 270

Val Tyr Lys Pro Leu Phe Glu Ala Val Gly Gly Ser Gly Gly Lys Thr
```

-continued

```
                275                 280                 285
Leu Glu Asp Val Phe Tyr Glu Arg Glu Val Gln Met Asn Val Leu Ala
    290                 295                 300

Phe Asn Arg Gln Phe His Tyr Gly Val Phe Tyr Ala Tyr Val Lys Leu
305                 310                 315                 320

Lys Glu Gln Glu Ile Arg Asn Ile Val Trp Ile Ala Glu Cys Ile Ser
                325                 330                 335

Gln Arg His Arg Thr Lys Ile Asn Ser Tyr Ile Pro Ile Leu
            340                 345                 350

<210> SEQ ID NO 15
<211> LENGTH: 487
<212> TYPE: PRT
<213> ORGANISM: Mus musculus

<400> SEQUENCE: 15

Met Val Ala Gly Arg Ser Arg Ala Arg Ser Pro Gly Ser Trp Leu Phe
1               5                   10                  15

Pro Gly Leu Trp Leu Leu Ala Val Gly Gly Pro Gly Ser Leu Leu Gln
            20                  25                  30

Ala Gln Glu Gln Pro Ser Cys Lys Lys Ala Phe Asp Leu Tyr Phe Val
        35                  40                  45

Leu Asp Lys Ser Gly Ser Val Ala Asn Asn Trp Ile Glu Ile Tyr Asn
50                  55                  60

Phe Val His Gln Leu Thr Glu Arg Phe Val Ser Pro Glu Met Arg Leu
65                  70                  75                  80

Ser Phe Ile Val Phe Ser Ser Gln Ala Thr Ile Ile Leu Pro Leu Thr
                85                  90                  95

Gly Asp Arg Tyr Lys Ile Gly Lys Gly Leu Glu Asp Leu Lys Ala Val
            100                 105                 110

Lys Pro Val Gly Glu Thr Tyr Ile His Glu Gly Leu Lys Leu Ala Asn
        115                 120                 125

Glu Gln Ile Gln Asn Ala Gly Gly Leu Lys Ala Ser Ser Ile Ile Ile
130                 135                 140

Ala Leu Thr Asp Gly Lys Leu Asp Gly Leu Val Pro Ser Tyr Ala Glu
145                 150                 155                 160

Asn Glu Ala Lys Lys Ser Arg Ser Leu Gly Ala Ser Val Tyr Cys Val
                165                 170                 175

Gly Val Leu Asp Phe Glu Gln Ala Gln Leu Glu Arg Ile Ala Asp Ser
            180                 185                 190

Lys Asp Gln Val Phe Pro Val Lys Gly Gly Phe Gln Ala Leu Lys Gly
        195                 200                 205

Ile Ile Asn Ser Ile Leu Ala Gln Ser Cys Thr Glu Ile Leu Glu Leu
210                 215                 220

Ser Pro Ser Ser Val Cys Val Gly Glu Lys Phe Gln Val Val Leu Thr
225                 230                 235                 240

Gly Arg Ala Val Thr Ser Ile Ser His Asp Gly Ser Val Leu Cys Thr
                245                 250                 255

Phe Thr Ala Asn Ser Thr Tyr Thr Lys Ser Glu Lys Pro Val Ser Ile
            260                 265                 270

Gln Pro Ser Ser Ile Leu Cys Pro Ala Pro Val Leu Asn Lys Asp Gly
        275                 280                 285

Glu Thr Leu Glu Val Ser Ile Ser Tyr Asn Asp Gly Lys Ser Ala Val
290                 295                 300
```

```
Ser Arg Ser Leu Thr Ile Thr Ala Thr Glu Cys Thr Asn Gly Ile Ala
305                 310                 315                 320

Ala Ile Val Ala Ile Leu Val Leu Leu Leu Leu Gly Ala Ala Leu
            325                 330                 335

Met Trp Trp Phe Trp Pro Leu Cys Cys Lys Val Ile Lys Asp Pro
                340                 345                 350

Pro Pro Pro Ser Ala Pro Met Glu Glu Glu Glu Asp Pro Leu
        355                 360                 365

Pro Asn Lys Lys Trp Pro Thr Val Asp Ala Ser Tyr Tyr Gly Gly Arg
    370                 375                 380

Gly Val Gly Gly Ile Lys Arg Met Glu Val Arg Trp Gly Asp Lys Gly
385                 390                 395                 400

Ser Thr Glu Glu Gly Ala Arg Leu Glu Lys Ala Lys Asn Ala Val Val
                405                 410                 415

Met Val Pro Glu Glu Ile Pro Ile Pro Ser Arg Pro Arg Pro
                420                 425                 430

Arg Pro Thr His Gln Ala Pro Gln Thr Lys Trp Tyr Thr Pro Ile Lys
                435                 440                 445

Gly Arg Leu Asp Ala Leu Trp Ala Leu Ile Met Lys Gln Tyr Asp Arg
    450                 455                 460

Val Ser Leu Met Arg Pro Gln Glu Gly Asp Glu Gly Arg Cys Ile Asn
465                 470                 475                 480

Phe Ser Arg Val Pro His Gln
                485

<210> SEQ ID NO 16
<211> LENGTH: 488
<212> TYPE: PRT
<213> ORGANISM: Homo sapiens

<400> SEQUENCE: 16

Met Val Ala Glu Arg Ser Pro Ala Arg Ser Pro Gly Ser Trp Leu Phe
1               5                   10                  15

Pro Gly Leu Trp Leu Leu Val Leu Ser Gly Pro Gly Gly Leu Leu Arg
            20                  25                  30

Ala Gln Glu Gln Pro Ser Cys Arg Arg Ala Phe Asp Leu Tyr Phe Val
        35                  40                  45

Leu Asp Lys Ser Gly Ser Val Ala Asn Asn Trp Ile Glu Ile Tyr Asn
    50                  55                  60

Phe Val Gln Gln Leu Ala Glu Arg Phe Val Ser Pro Glu Met Arg Leu
65                  70                  75                  80

Ser Phe Ile Val Phe Ser Ser Gln Ala Thr Ile Ile Leu Pro Leu Thr
                85                  90                  95

Gly Asp Arg Gly Lys Ile Ser Lys Gly Leu Glu Asp Leu Lys Arg Val
            100                 105                 110

Ser Pro Val Gly Glu Thr Tyr Ile His Glu Gly Leu Lys Leu Ala Asn
        115                 120                 125

Glu Gln Ile Gln Lys Ala Gly Gly Leu Lys Thr Ser Ser Ile Ile Ile
    130                 135                 140

Ala Leu Thr Asp Gly Lys Leu Asp Gly Leu Val Pro Ser Tyr Ala Glu
145                 150                 155                 160

Lys Glu Ala Lys Ile Ser Arg Ser Leu Gly Ala Ser Val Tyr Cys Val
                165                 170                 175

Gly Val Leu Asp Phe Glu Gln Ala Gln Leu Glu Arg Ile Ala Asp Ser
            180                 185                 190
```

```
Lys Glu Gln Val Phe Pro Val Lys Gly Gly Phe Gln Ala Leu Lys Gly
            195                 200                 205

Ile Ile Asn Ser Ile Leu Ala Gln Ser Cys Thr Glu Ile Leu Glu Leu
            210                 215                 220

Gln Pro Ser Ser Val Cys Val Gly Glu Glu Phe Gln Ile Val Leu Ser
225                 230                 235                 240

Gly Arg Gly Phe Met Leu Gly Ser Arg Asn Gly Ser Val Leu Cys Thr
                245                 250                 255

Tyr Thr Val Asn Glu Thr Tyr Thr Thr Ser Val Lys Pro Val Ser Val
                260                 265                 270

Gln Leu Asn Ser Met Leu Cys Pro Ala Pro Ile Leu Asn Lys Ala Gly
            275                 280                 285

Glu Thr Leu Asp Val Ser Val Ser Phe Asn Gly Gly Lys Ser Val Ile
            290                 295                 300

Ser Gly Ser Leu Ile Val Thr Ala Thr Glu Cys Ser Asn Gly Ile Ala
305                 310                 315                 320

Ala Ile Ile Val Ile Leu Val Leu Leu Leu Leu Gly Ile Gly Leu
                325                 330                 335

Met Trp Trp Phe Trp Pro Leu Cys Cys Lys Val Val Ile Lys Asp Pro
                340                 345                 350

Pro Pro Pro Pro Ala Pro Ala Pro Lys Glu Glu Glu Glu Glu Pro Leu
            355                 360                 365

Pro Thr Lys Lys Trp Pro Thr Val Asp Ala Ser Tyr Tyr Gly Gly Arg
            370                 375                 380

Gly Val Gly Gly Ile Lys Arg Met Glu Val Arg Trp Gly Asp Lys Gly
385                 390                 395                 400

Ser Thr Glu Glu Gly Ala Arg Leu Glu Lys Ala Lys Asn Ala Val Val
                405                 410                 415

Lys Ile Pro Glu Glu Thr Glu Glu Pro Ile Arg Pro Arg Pro Pro Arg
            420                 425                 430

Pro Lys Pro Thr His Gln Pro Pro Gln Thr Lys Trp Tyr Thr Pro Ile
            435                 440                 445

Lys Gly Arg Leu Asp Ala Leu Trp Ala Leu Leu Arg Arg Gln Tyr Asp
            450                 455                 460

Arg Val Ser Leu Met Arg Pro Gln Glu Gly Asp Glu Gly Arg Cys Ile
465                 470                 475                 480

Asn Phe Ser Arg Val Pro Ser Gln
                485
```